(12) United States Patent
Carson et al.

(10) Patent No.: US 7,435,822 B2
(45) Date of Patent: Oct. 14, 2008

(54) 3-(DIHETEROARYLMETHYLENE)-8-AZABICYCLO[3.2.1]OCTANE AND 3-((ARYL)(HETEROARYL)METHYLENE)-8-AZABICYCLO[3.2.1]OCTANE DERIVATIVES

(75) Inventors: John R. Carson, Norristown, PA (US); Jung S. Lee, McLean, VA (US)

(73) Assignee: Janssen Pharmaceutica N.V., Beerse (BE)

( * ) Notice: Subject to any disclaimer, the term of this patent is extended or adjusted under 35 U.S.C. 154(b) by 59 days.

(21) Appl. No.: 11/048,976

(22) Filed: Feb. 2, 2005

(65) Prior Publication Data

US 2005/0171099 A1 Aug. 4, 2005

Related U.S. Application Data

(60) Provisional application No. 60/541,408, filed on Feb. 3, 2004.

(51) Int. Cl.
*C07D 401/00* (2006.01)
*C07D 405/00* (2006.01)
*C07D 409/00* (2006.01)
*C07D 411/00* (2006.01)
*C07D 413/00* (2006.01)

(52) U.S. Cl. .................................................. 546/125
(58) Field of Classification Search ............... 546/125; 514/304
See application file for complete search history.

(56) References Cited

U.S. PATENT DOCUMENTS 2,800,482 A * 7/1957 Zirkle ........................ 546/124
2005/0004163 A1 * 1/2005 Coats et al. ................. 514/304

FOREIGN PATENT DOCUMENTS

WO WO 93/15062 A1 5/1993
WO WO 97/23466 A1 7/1997
WO WO 98/28270 A1 7/1998
WO WO 98/28275 A1 7/1998

OTHER PUBLICATIONS

Zirkle et al., Journla of Medicinal & Pharmaceutical Chemistry, "3-substituted tropane derivatives. III. 3-substituted tropane carbinols, alkenes, and alkanes", 1962, vol. 5, pp. 341-356.*
Gutkowska, B. et al., "Synthesis of Some Amide Derivatives of 3-Aminotropane With Potential Pharmacological Activity 1". *Acta Polon. Pharm.*, 1984, pp. 613-617, vol. 41, No. 6.
Boyd, R. E. et al., "Synthesis and Binding Affinites of 4-Diarylaminotropanes, a New Class of Delta Opioid Agonists." *Bio. Med. Chem. Lett.*, 2000, pp. 1109-1111, vol. 10.
Thomas, J. B. et al., "4-[(8-Alkly-8-azabicyclo[3.2.1.]octyl-3-yl)-3-arylanilino]-N,N-diethylbenzamides: High Affinity, Selective Ligands for the Delta Oploid Receptor Illustrate Factors Important to Antagonist Activity." *Bio. Med. Chem. Lett.*, 2000, pp. 1281-1284, vol. 10.
Coats, S.J. et al.: "Parallel methods for the preparation and SAR exploration of N-ethyl-4-[(8-alkyl-8-aza-bicyclo[3.2.1]-oct-3-ylidene)-aryl-methyl-]-benzamides, powerful mu and delta opiod agonists"; Bioorg. & Med. Chem. Letters (2004) 14:5493-5498.
Munson, P.J. et al.: "Ligand: A Versatile Computerized Approach for Characterization of Ligand-Binding Systems"; Analytical Biochem. (1980) 107(1): 220-239.
Still, W. C. et al.: "Rapid Chromatographic Technique for Preparative Separations with Moderate Resolution"; J. Org. Chem. (1978) 43(14): 2923-2925.

* cited by examiner

*Primary Examiner*—Janet L. Andres
*Assistant Examiner*—Niloofar Rahmani

(57) ABSTRACT

This invention is directed to 3-(diheteroarylmethylene)-8-azabicyclo[3.2.1] octane and 3-((aryl)(heteroaryl)methylene)-8-azabicyclo[3.2.1] octane derivatives useful as δ-opioid, μ-opioid, or δ-opioid and μ-opioid receptor receptor modulators. Depending on their agonist or antagonist effect, the compounds are useful analgesics, immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases.

12 Claims, No Drawings

3-(DIHETEROARYLMETHYLENE)-8-AZABICYCLO[3.2.1]OCTANE AND 3-((ARYL)(HETEROARYL)METHYLENE)-8-AZABICYCLO[3.2.1]OCTANE DERIVATIVES

CROSS-REFERENCE TO RELATED APPLICATIONS

This application claims priority to U.S. Provisional Application No. 60/541,408 filed Feb. 3, 2004 which is hereby incorporated by reference in its entirety.

STATEMENT REGARDING FEDERALLY SPONSORED RESEARCH OR DEVELOPMENT

The research and development of the invention described below was not federally sponsored.

BACKGROUND OF THE INVENTION

WO 97/23466 describes compounds as having an analgesic effect of a general and one preferred formula:

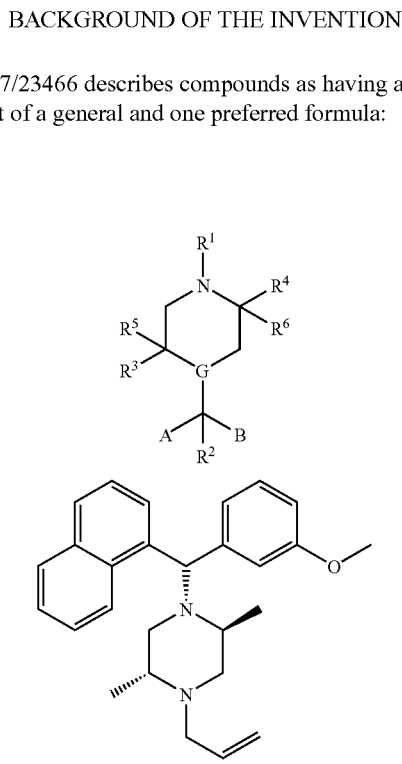

WO 98/28270 describes compounds as having an analgesic effect of a general and one preferred formula:

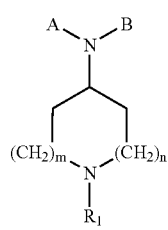

WO 98/28275 describes compounds as having an analgesic effect of a general and one preferred formula:

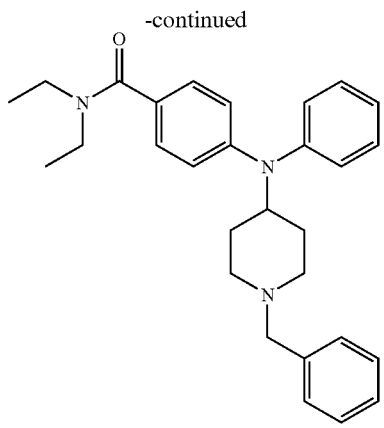

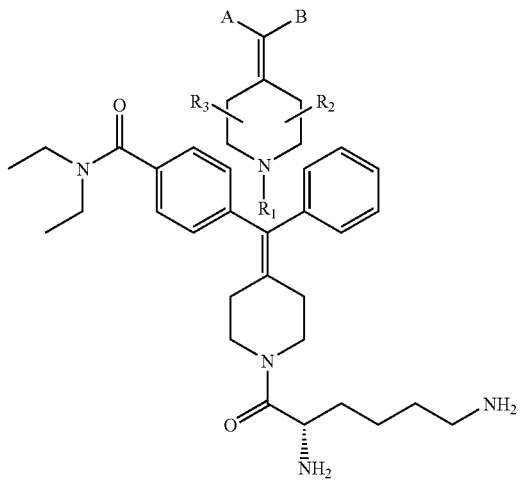

Amide derivatives of 3-aminotropane have been prepared and described as having potential pharmacological activity (Gutkowska, B., et al., Acta Pol. Pharm., 1984, 41(6), 613-617), of the formula:

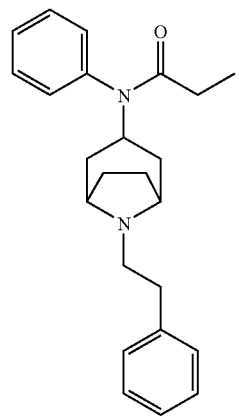

WO 93/15062 describes compounds as delta-opioid (δ-opioid) and mu-opioid (μ-opioid) receptor agonists of (approximately) the general formula:

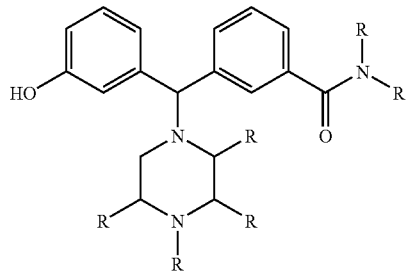

The synthesis and binding affinities for 4-Diarylaminotropane compounds as δ-opioid agonists have been described (Boyd, R. E., Carson, J. R., Codd, E. E., Gauthier, A. D., Neilson, L. A and Zhang, S-P., *Bioorg. Med. Chem. Lett.*, 2000, 10, 1109-1111) of the general formula:

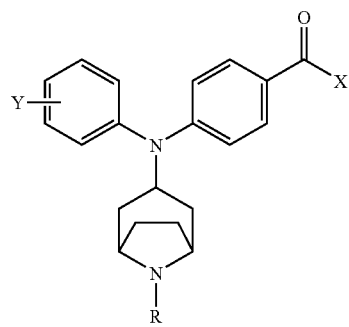

wherein R is hydrogen, methyl, propyl, hexyl, 2-ethylbutyl, allyl, 3,3-dimethallyl, cyclohexylmethyl, phenethyl, phenylpropyl, 2,2-diphenylethyl, 3,4-dimethoxyphenethyl, 4-fluorophenethyl, 2-furylmethyl, 3,4-methylenedioxybenzyl, cyano and X is N,N-dimethylamino, N,N-diethylamino, N,N-dipropylamino, N-methyl-N-ethylamino, N-methyl-N-propylamino, N-methyl-N-phenylamino, N-ethyl-N-(4-methyl)benzylamino, N-butyl-N-ethylamino, N-butyl-N-propylamino, [N-ethyl-N-(2-methyl)allyl]amino, hydroxy, O-t-butyl and 1-pyrrolidinyl; and, Y is hydrogen, methoxy and methylthio.

Other selective 4-[(8-alkyl-8-azabicyclo[3.2.1] octyl-3-yl)-3-arylanilino]-N,N-diethylbenzamide δ-opioid ligands have also been described (Thomas, J. B., Atkinson, R. N., Rothman, R. B., Burgess, J. P., Mascarella, S. W., Dersch, C. M., Xu, H. and Carroll, F. I., *Bioorg. Med. Chem. Lett.*, 2000, 10, 1281-1284).

The present invention is directed to compounds useful as delta-opioid and mu-opioid receptor modulators. More particularly, the present invention is directed to delta-opioid and mu-opioid receptor modulators.

SUMMARY OF THE INVENTION

The present invention is directed to a compound of formula I or II

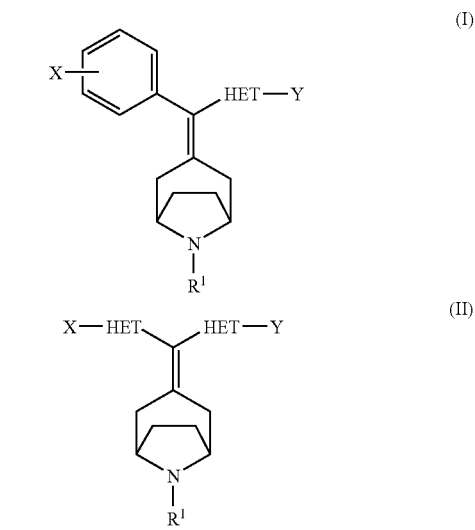

Wherein

HET is a 5-membered cyclic heteroalkanyl containing 1-2 heteroatoms independently selected from the group consisting of N, O and S; a 6-membered cyclic heteroalkanyl containing 1-3 heteroatoms independently selected from the group consisting of N, O and S; a 5-membered heteroaryl containing 1-2 heteroatoms independently selected from the group consisting of N, O and S; or a 6-membered heteroaryl containing 1-3 heteroatoms independently selected from the group consisting of N, O and S; wherein the point of attachment of HET to the rest of the molecule is through a ring carbon atom;

X and Y are one to three substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylcarbonylamino, $C_{1-6}$alkanylthio, $C_{1-6}$alkanylsulfonyl, halogen, hydroxy, cyano, hydroxycarbonyl, tetrazolyl, fluoroalkanyl and fluoroalkanyloxy; or X and Y taken together may form a bridge of 1 or 2 atoms selected from the group consisting of O, S, $CH_2$ and —N($R^2$)— wherein $R^2$ is $C_{1-6}$alkyl;

$R^1$ is selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, formyl, thioformyl, carbamidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoroalkanyl, thioureido, and fluoroalkanyloxy; alternatively, when phenyl and heteroaryl are optionally substituted with two substituents attached to adjacent carbon atoms, the two substituents can together form a single fused moiety; wherein the fused moiety is selected from the group consisting of —$(CH_2)_{3-5}$— and —$O(CH_2)_{1-3}O$—;

and pharmaceutically acceptable enantiomers, diastereomers and salts thereof.

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

"Fluorinated alkyl" refers to a saturated branched or straight chain hydrocarbon radical derived by removal of 1 hydrogen atom from the parent alkane; the parent alkane contains from 1 to 6 carbon atoms with 1 or more hydrogen atoms substituted with fluorine atoms up to and including substitution of all hydrogen atoms with fluorine. Preferred fluorinated alkyls include trifluoromethyl substituted alkyls and perfluorinated alkyls; more preferred fluorinated alkyls include trifluoromethyl, perfluoroethyl, 2,2,2-trifluoroethyl, perfluoropropyl, 3,3,3-trifluoroprop-1-yl, 3,3,3-trifluoroprop-2-yl, 1,1,1,3,3,3-hexafluoroprop-2-yl; a particularly preferred fluorinated alkyl is trifluoromethyl.

"Fluorinated alkanyloxy" refers to a radical derived from a fluorinated alkyl radical attached to an oxygen atom with the oxygen atom having one open valence for attachment to a parent structure.

"Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_{1-8}$) alkyl, with ($C_{1-3}$) being particularly preferred.]

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc., and the like. In preferred embodiments, the alkanyl groups are ($C_{1-8}$)alkanyl, with ($C_{1-3}$) being particularly preferred.

"Alkenyl:" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1 -yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is ($C_{2-8}$)alkenyl, with ($C_{2-3}$) being particularly preferred.

"Alkynyl:" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is ($C_{2-8}$)alkynyl, with ($C_{2-3}$) being particularly preferred.

"Alkyldiyl:" refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers can form bonds with the same or different atoms. Typical alkyldiyls include, but are not limited to methandiyl; ethyidiyls such as ethan-1,1-diyl, ethan-1,2-diyl, ethen-1,1-diyl, ethen-1,2-diyl; propyidiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methylprop-2-en-1,1-diyl, buta-1,3-dien-1,1-diyl, buta-1,3-dien-1,2-diyl, buta-1,3-dien-1,3-diyl, buta-1,3-dien-1,4-diyl, cyclobut-1 -en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In preferred embodiments, the alkyldiyl group is ($C_{1-8}$)alkyldiyl, with ($C_{1-8}$) being particularly preferred. Also preferred are saturated acyclic alkandiyl radicals in which the radical centers are at the terminal carbons, e.g., methandiyl; ethan-1,2-diyl; propan-1,3-diyl; butan-1,4-diyl; and the like (also referred to as alkylenos, as defined infra).

"Vic Alkyldiyl:" refers to a saturated or unsaturated, branched, straight-chain or cyclic hydrocarbon radical having two adjacent monovalent radical centers derived by the removal of one hydrogen atom from each of two adjacent carbon atoms of a parent alkane, alkene or alkyne. The two monovalent radical centers can form bonds with the same or different atom(s). Typical vic alkyldiyls include, but are not limited to vic ethyldiyls such as ethan-1,2-diyl, ethen-1,2- diyl; vic propyldiyls such as propan-1,2-diyl, cyclopropan-1,2-diyl, prop-1-en-1,2-diyl, prop-2-en-1,2-diyl, cycloprop-1-en-1,2-diyl, etc.; vic butyldiyls such as butan-1,2-diyl, 2-methyl-propan-1,2-diyl, cyclobutan-1,2-diyl, but-1-en-1,2-diyl, cyclobut-1-en-1,2-diyl, buta-1,3-dien-1,2-diyl, cyclobuta-1,3-dien-1,2-diyl, but-3-yn-1,2-diyl, etc.; and the like. Where specific levels of saturation are intended, the nomenclature vic alkandiyl, vic alkendiyl and/or vic alkyndiyl is used. In preferred embodiments, the vic alkyldiyl group is $(C_{2-8})$vic alkyldiyl, with $(C_{2-3})$ being particularly preferred.

"Gem Alkyldiyl:" refers to a saturated or unsaturated, branched, straight-chain or cyclic hydrocarbon radical having one divalent radical center derived by the removal of two hydrogen atoms from a single carbon atom of a parent alkane, alkene or alkyne. The divalent radical center forms bonds with two different atoms. Typical gem alkyldiyls include, but are not limited to gem methanyldiyl; gem ethyldiyls such as ethan-1,1-diyl,ethen-1,1-diyl; gem propyldiyls such as propan-1,1-diyl, propan-2,2-diyl, cyclopropan-1,1-diyl, prop-1-en-1,1-diyl, cycloprop-2-en-1,1-diyl, prop-2-yn-1,1-diyl, etc.; butyldiyls such as butan-1,1-diyl, butan-2,2-diyl, 2-methyl-propan-1,2-diyl, cyclobutan-1,1-diyl, but-1-en-1,1-diyl, 2-methyl-prop-1-en-1,1-diyl, 2-methyl-prop-2-en-1,1-diyl, cyclobut-2-en-1,1-diyl, buta-1,3-dien-1,1-diyl, etc.; and the like. Where specific levels of saturation are intended, the nomenclature gem alkandiyl, gem alkendiyl and/or gem alkyndiyl is used. In preferred embodiments, the gem alkyldiyl group is $(C_{1-6})$gem alkyldiyl, with $(C_{1-3})$ being particularly preferred.

"Alkyleno:" refers to a saturated or unsaturated, straight-chain or branched acyclic bivalent hydrocarbon bridge radical derived by the removal of one hydrogen atom from each of the two terminal carbon atoms of an acyclic parent alkane, alkene or alkyne. Typical alkyleno groups include, but are not limited to, methano; ethylenos such as ethano, etheno, ethyno; propylenos such as propano, propeno, prop-1,2-dieno, propyno, etc.; butylenos such as butano, 2-methyl-propano, but-1-eno, but-2-eno, 2-methyl-prop-1-eno, 2-methanylidine-propano, but-1,3-dieno, but-1-yno, but-2-yno, but-1,3-diyno, etc.; and the like. Where specific levels of saturation are intended, the nomenclature alkano, alkeno and/or alkyno is used. In preferred embodiments, the alkyleno group is $(C_{1-8})$alkyleno, with $(C_{1-3})$ being particularly preferred. Also preferred are straight-chain saturated alkano radicals, e.g., methano, ethano, propano, butano, and the like.

"Alkylidene:" refers to a saturated or unsaturated, branched, straight-chain or cyclic divalent hydrocarbon radical derived by removal of two hydrogen atoms from the same carbon atom of a parent alkane, alkene or alkyne. The divalent radical center forms a double bond with a single atom. Typical alkylidene radicals include, but are not limited to, methanylidene, ethylidenes such as ethanylidene, ethenylidene; propylidenes such as propan-1-ylidene, propan-2-ylidine, cyclopropan-1-ylidene, prop-1-en-1-ylidene, prop-2-en-1-ylidene, cycloprop-2-en-1-ylidene, etc.; butylidenes such as butan-1-ylidene, butan-2-ylidine, 2-methyl-propan-1-ylidene, cyclobutan-1-ylidene, but-1-en-1-ylidene, but-2-en-1-ylidene, but-3-en-1-ylidene, buta-1,3-dien-1-ylidene; cyclobut-2-en-1-ylidene, etc.; and the like. Where specific levels of saturation are intended, the nomenclature alkanylidene, alkenylidene and/or alkynylidene is used. In preferred embodiments, the alkylidene group is $(C_{1-8})$alkylidene, with $(C_{1-3})$ being particularly preferred. Also preferred are acyclic saturated alkanylidene radicals in which the divalent radical is at a terminal carbon, e.g., methanylidene, ethan-1-ylidene, propan-1-ylidene, butan-1-ylidene, 2-methyl-propan-1-ylidene, and the like.

"Alkylidyne:" refers to a saturated or unsaturated, branched or straight-chain trivalent hydrocarbon radical derived by removal of three hydrogen atoms from the same carbon atom of a parent alkane, alkene or alkyne. The trivalent radical center forms a triple bond with a single atom. Typical alkylidyne radicals include, but are not limited to, methanylidyne; ethanylidyne; propylidynes such as propan-1-ylidyne, prop-2-en-1-ylidyne, prop-2-yn-1-ylidine; butylidynes such as butan-1-ylidyne, 2-methyl-propan-1-ylidyne, but-2-en-1-ylidyne, but-3-en-1-ylidyne, buta-2,3-dien-1-ylidyne, but-2-yn-1-ylidyne, but-3-yn-1-ylidyne, etc.; and the like. Where specific levels of saturation are intended, the nomenclature alkanylidyne, alkenylidyne and/or alkynylidyne is used. In preferred embodiments, the alkylidyne group is $(C_{1-8})$ alkylidyne, with $(C_{1-3})$ being particularly preferred. Also preferred are saturated alkanylidyne radicals, e.g., methanylidyne, ethanylidyne, propan-1-ylidyne, butan-1-ylidyne, 2-methyl-propan-1-ylidyne, and the like.

"Heteroalkyl, Heteroalkanyl, Heteroalkenyl, Heteroalkynyl, Heteroalkylidene. Heteroalkylidyne, Heteroalkyldiyl, Vic Heteralkyldiyl, Gem Heteroalkyldiyl, Heteroalkyleno and Heteroalkyldiylidene:" refer to alkyl, alkanyl, alkenyl, alkynyl, alkylidene, alkylidyne, alkyldiyl, vic alkyldiyl, gem alkyldiyl, alkyleno and alkyldiylidene radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkyl, heteroalkanyl, heteroalkenyl, heteroalkynyl, heteroalkylidene, heteroalkylidyne, heteroalkyldiyl, vic heteroalkyldiyl, gem heteroalkyldiyl, heteroalkyleno and heteroalkyldiylidene radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimmino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or $(C_1$-$C_6)$alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, benzene, fluorene, indane, indene, naphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from benzene, fluorene, indane, indene, naphthalene, and the like. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. [In preferred embodiments, the arylalkyl group is $(C_{6-26})$ arylalkyl, e.g., the alkanyl, alkenyl or alkynyl moiety of the arylalkyl group is $(C_{1-6})$ and the aryl moiety is $(C_{5-20})$. In particularly preferred embodiments the arylalkyl group is $(C_{6-13})$, e.g., the alkanyl, alkenyl or alkynyl moiety of the arylalkyl group is $(C_{1-3})$ and the aryl moiety is $(C_{5-10})$. Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyl; ethanyloxy; propanyloxy groups such as propan-1-yloxy ($CH_3CH_2CH_2O—$), propan-2-yloxy (($CH_3$)$_2$CHO—), cyclopropan-1-yloxy, etc.; butyanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are $(C_{1-8})$alkanyloxy groups, with $(C_{1-3})$ being particularly preferred.

"Parent Heteroaromatic Ring System:" refers to a parent aromatic ring system in which one or more carbon atoms are each independently replaced with a heteroatom. Typical heteratoms to replace the carbon atoms include, but are not limited to, N, P, O, S, Si etc. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, furan, imidazole, isothiazole, isoxazole, oxadiazole, oxazole, purine, pyran, pyrazine, pyrazole, pyridazine, pyridine, pyrimidine, pyrrole, pyrrolizine, tetrazole, thiadiazole, thiazole, thiophene, triazole, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from furan, imidazole, isothiazole, isoxazole, oxadiazole, oxazole, purine, pyran, pyrazine, pyrazole, pyridazine, pyridine, pyrimidine, pyrrole, pyrrolizine, tetrazole, thiadiazole, thiazole, thiophene, triazole and the like.

"Substituted:" refers to a radical in which one or more hydrogen atoms are each independently replaced with the same or different substituent(s). Typical substituents include, but are not limited to, —X, —R, —O—, =O, —OR, —O—OR, —SR, —S—, =S, —NRR, =NR, —CX$_3$, —CN, —OCN, —SCN, —NCO, —NCS, —NO, —NO$_2$, =N$_2$, —N$_3$, —NHOH, —S(O)$_2$O—, —S(O)$_2$OH, —S(O)$_2$R, —P(O)(O$^-$)$_2$, —P(O)(OH)$_2$, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, $C_{1-8}$alkyl, $C_{1-8}$alkanyloxy, fluorinated alkanyloxy, fluorinated alkyl, $C_{1-8}$alkylthio, $C_{3-8}$cycloalkyl, $C_{3-8}$cycloalkanyloxy, nitro, amino, $C_{1-8}$alkylamino, $C_{1-8}$dialkylamino, $C_{3-8}$cycloalkylamino, cyano, carboxy, $C_{1-7}$alkanyloxycarbonyl, $C_{1-7}$alkylcarbonyloxy, formyl, carbamoyl, phenyl, aroyl, carbamoyl, amidino, ($C_{1-8}$alkylamino)carbonyl, (arylamino)carbonyl and aryl($C_{1-8}$alkyl)carbonyl "Aroyl" refers to arylacyl substituents.

"Acyl" refers to alkylcarbonyl substituents.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenyl$C_{1-6}$alkanylaminocarbonyl$C_{1-6}$alkyl" substituent refers to a group of the formula

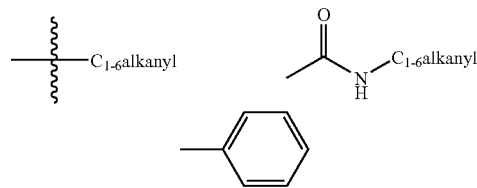

The present invention is directed to a compound of formula I or II

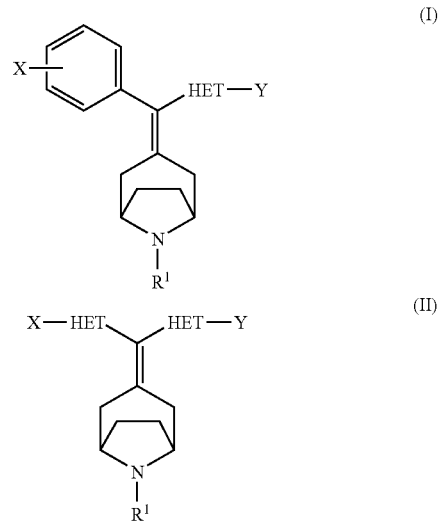

Wherein
HET is a 5-membered cyclic heteroalkanyl containing 1-2 heteroatoms independently selected from the group consisting of N, O and S; a 6-membered cyclic heteroalkanyl containing 1-3 heteroatoms independently selected from the group consisting of N, O and S; a 5-membered heteroaryl containing 1-2 heteroatoms independently selected from the group consisting of N, O and S; or a 6-membered heteroaryl containing 1-3 heteroatoms independently selected from the group consisting of N, O and S; wherein the point of attachment of HET to the rest of the molecule is through a ring carbon atom;

X and Y are one to three substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, C$_{1-6}$alkanylcarbonylamino, C$_{1-6}$alkanylthio, C$_{1-6}$alkanylsulfonyl, halogen, hydroxy, cyano, hydroxycarbonyl, tetrazolyl, fluoroalkanyl and fluoroalkanyloxy; or X and Y taken together may form a bridge of 1 or 2 atoms selected from the group consisting of O, S, CH$_2$ and —N(R$^2$)— wherein R$^2$ is C$_{1-6}$alkyl;

R$^1$ is selected from the group consisting of hydrogen, C$_{1-8}$alkanyl, halo$_{1-3}$(C$_{1-8}$)alkanyl, C$_{2-8}$alkenyl, C$_{2-8}$alkynyl, C$_{3-8}$cycloalkanyl, cycloalkanyl(C$_{1-8}$)alkanyl, C$_{1-8}$alkanyloxy(C$_{1-8}$)alkanyl, C$_{1-8}$alkanylthio(C$_{1-8}$)alkanyl, hydroxyC$_{1-8}$alkanyl, formyl, thioformyl, carbamimidoyl, phenylimino(C$_{1-8}$)alkanyl, phenyl(C$_{1-8}$)alkanyl, phenyl(C$_{1-8}$)alkenyl, phenyl(C$_{1-8}$)alkynyl, naphthyl(C$_{1-8}$)alkanyl and heteroaryl(C$_{1-8}$)alkanyl; wherein phenyl, naphthyl and heteroaryl are optionally substituted with one to three substituents independently selected from the group consisting of C$_{1-6}$alkanyl, C$_{2-6}$alkenyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanylcarbonylamino, C$_{1-6}$alkanylthio, C$_{1-6}$alkanylsulfonyl, halogen, hydroxy, cyano, fluoroalkanyl, thioureido, and fluoroalkanyloxy; alternatively, when phenyl and heteroaryl are optionally substituted with two substituents attached to adjacent carbon atoms, the two substituents can together form a single fused moiety; wherein the fused moiety is selected from the group consisting of —(CH$_2$)$_{3-5}$— and —O(CH$_2$)$_{1-3}$O—;

and pharmaceutically acceptable enantiomers, diastereomers and salts thereof.

Embodiments of the present invention include those wherein the compound is (a) a compound of formula (I);
(b) a compound of formula (II);
(c) a compound of formula (I) wherein HET is thienyl;
(d) a compound of formula (I) wherein HET is thien-3-yl;
(e) a compound of formula (I) wherein X is hydroxyl;
(f) a compound of formula (I) wherein Y is hydrogen;
(g) a compound of formula (I) wherein R$^1$ is heteroaryl(C$_{1-8}$)alkanyl optionally substituted with one to three substituents independently selected from the group consisting of C$_{1-6}$alkanyl, C$_{2-6}$alkenyl, C$_{1-6}$alkanyloxy, amino, C$_{1-6}$alkanylamino, di(C$_{1-6}$alkanyl)amino, C$_{1-6}$alkanylcarbonyl, C$_{1-6}$alkanylcarbonyloxy, C$_{1-6}$alkanylcarbonylamino, C$_{1-6}$alkanylthio, C$_{1-6}$alkanylsulfonyl, halogen, hydroxy, cyano, fluoroalkanyl, thioureido, and fluoroalkanyloxy; in particular, a compound of formula (I) wherein said heteroaryl is thienyl, and more particularly, wherein said thienyl is unsubstituted, and also in particular, wherein said thienyl is thien-2-yl; and
(h) combinations of (a) through (g), above.

Embodiments of the present invention also include a compound selected from the group consisting of 3-(Phenyl-thiophen-3-yl-methylene)-8-aza-bicyclo[3.2.1]octane;
8-(3-Methyl-but-2-enyl)-3-(phenyl-thiophen-3-yl-methylene)-8-aza-bicyclo[3.2.1]octane;
8-Phenethyl-3-(phenyl-thiophen-3-yl-methylene)-8-aza-bicyclo[3.2.1]octane;
8-(2-Methyl-benzyl)-3-(phenyl-thiophen-3-yl-methylene)-8-aza-bicyclo[3.2.1]octane;
8-(2-Chloro-benzyl)-3-(phenyl-thiophen-3-yl-methylene)-8-aza-bicyclo[3.2.1]octane;
3-(Phenyl-thiophen-3-yl-methylene)-8-thiophen-2-ylmethyl-8-aza-bicyclo[3.2.1]octane;
8-(3-Methyl-thiophen-2-ylmethyl)-3-(phenyl-thiophen-3-yl-methylene)-8-aza-bicyclo[3.2.1]octane;
8-(5-Methyl-thiophen-2-ylmethyl)-3-(phenyl-thiophen-3-yl-methylene)-8-aza-bicyclo[3.2.1]octane;
3-[(3-Methoxy-phenyl)-thiophen-3-yl-methylene]-8-aza-bicyclo[3.2.1]octane;
8-Allyl-3-[(3-methoxy-phenyl)-thiophen-3-yl-methylene]-8-aza-bicyclo[3.2.1]octane;
3-[(3-Methoxy-phenyl)-thiophen-3-yl-methylene]-8-(3-methyl-but-2-enyl)-8-aza-bicyclo[3.2.1]octane;
3-[(3-Methoxy-phenyl)-thiophen-3-yl-methylene]-8-phenethyl-8-aza-bicyclo[3.2.1]octane;
3-[(3-Methoxy-phenyl)-thiophen-3-yl-methylene]-8-(2-methyl-benzyl)-8-aza-bicyclo[3.2.1]octane;
8-(2-Chloro-benzyl)-3-[(3-methoxy-phenyl)-thiophen-3-yl-methylene]-8-aza-bicyclo[3.2.1]octane;
3-[(3-Methoxy-phenyl)-thiophen-3-yl-methylene]-8-thiophen-2-ylmethyl-8-aza-bicyclo[3.2.1]octane;
3-[(3-Methoxy-phenyl)-thiophen-3-yl-methylene]-8-(3-methyl-thiophen-2-ylmethyl)-8-aza-bicyclo[3.2.1]octane;
3-[(3-Methoxy-phenyl)-thiophen-3-yl-methylene]-8-(5-methyl-thiophen-2-ylmethyl)-8-aza-bicyclo[3.2.1]octane;
3-[(8-Aza-bicyclo[3.2.1]oct-3-ylidene)-thiophen-3-yl-methyl]-phenol;
3-{[8-(3-Methyl-but-2-enyl)-8-aza-bicyclo[3.2.1]oct-3-ylidene]-thiophen-3-yl-methyl}-phenol;
3-[(8-Allyl-8-aza-bicyclo[3.2.1]oct-3-ylidene)-thiophen-3-yl-methyl]-phenol;
3-[(8-Phenethyl-8-aza-bicyclo[3.2.1]oct-3-ylidene)-thiophen-3-yl-methyl]-phenol;
3-{[8-(2-Methyl-benzyl)-8-aza-bicyclo[3.2.1]oct-3-ylidene]-thiophen-3-yl-methyl}-phenol;
3-{[8-(2-Chloro-benzyl)-8-aza-bicyclo[3.2.1]oct-3-ylidene]-thiophen-3-yl-methyl}-phenol;
3-[Thiophen-3-yl-(8-thiophen-2-ylmethyl-8-aza-bicyclo[3.2.1]oct-3-ylidene)-methyl]-phenol;
3-{[8-(3-Methyl-thiophen-2-ylmethyl)-8-aza-bicyclo[3.2.1]oct-3-ylidene]-thiophen-3-yl-methyl}-phenol;
3-{[8-(5-Methyl-thiophen-2-ylmethyl)-8-aza-bicyclo[3.2.1]oct-3-ylidene]-thiophen-3-yl-methyl}-phenol;
3-[(4-Methoxy-phenyl)-thiophen-3-yl-methylene]-8-aza-bicyclo[3.2.1]octane;
3-[(4-Methoxy-phenyl)-thiophen-3-yl-methylene]-8-(3-methyl-but-2-enyl)-8-aza-bicyclo[3.2.1]octane;
3-[(4-Methoxy-phenyl)-thiophen-3-yl-methylene]-8-phenethyl-8-aza-bicyclo[3.2.1]octane;
3-[(4-Methoxy-phenyl)-thiophen-3-yl-methylene]-8-(2-methyl-benzyl)-8-aza-bicyclo[3.2.1]octane;
8-(2-Chloro-benzyl)-3-[(4-methoxy-phenyl)-thiophen-3-yl-methylene]-8-aza-bicyclo[3.2.1]octane;
3-[(4-Methoxy-phenyl)-thiophen-3-yl-methylene]-8-thiophen-2-ylmethyl-8-aza-bicyclo[3.2.1]octane;
3-[(4-Methoxy-phenyl)-thiophen-3-yl-methylene]-8-(3-methyl-thiophen-2-ylmethyl)-8-aza-bicyclo[3.2.1]octane;
3-[(4-Methoxy-phenyl)-thiophen-3-yl-methylene]-8-(5-methyl-thiophen-2-ylmethyl)-8-aza-bicyclo[3.2.1]octane;
4-{[8-(3-Methyl-but-2-enyl)-8-aza-bicyclo[3.2.1]oct-3-ylidene]-thiophen-3-yl-methyl}-phenol;
4-[(8-Phenethyl-8-aza-bicyclo[3.2.1]oct-3-ylidene)-thiophen-3-yl-methyl]-phenol;
4-{[8-(2-Methyl-benzyl)-8-aza-bicyclo[3.2.1]oct-3-ylidene]-thiophen-3-yl-methyl}-phenol;
4-{[8-(2-Chloro-benzyl)-8-aza-bicyclo[3.2.1]oct-3-ylidene]-thiophen-3-yl-methyl}-phenol;
4-[Thiophen-3-yl-(8-thiophen-2-ylmethyl-8-aza-bicyclo[3.2.1]oct-3-ylidene)-methyl]-phenol;

4-{[8-(3-Methyl-thiophen-2-ylmethyl)-8-aza-bicyclo[3.2.1]oct-3-ylidene]-thiophen-3-yl-methyl}-phenol; and
4-{[8-(5-Methyl-thiophen-2-ylmethyl)-8-aza-bicyclo[3.2.1]oct-3-ylidene]-thiophen-3-yl-methyl}-phenol.

and pharmaceutically acceptable enantiomers, solvates, diastereomers and salts thereof.

Embodiments of the present invention also include a compound selected from the group consisting of
3-(Phenyl-thiophen-3-yl-methylene)-8-aza-bicyclo[3.2.1]octane;
8-(3-Methyl-but-2-enyl)-3-(phenyl-thiophen-3-yl-methylene)-8-aza-bicyclo[3.2.1]octane;
8-Phenethyl-3-(phenyl-thiophen-3-yl-methylene)-8-aza-bicyclo[3.2.1]octane;
8-(2-M ethyl-benzyl)-3-(phenyl-thiophen-3-yI-methylene)-8-aza-bicyclo[3.2.1]octane;
8-(2-Chloro-benzyl)-3-(phenyl-thiophen-3-yl-methylene)-8-aza-bicyclo[3.2.1]octane;
3-(Phenyl-thiophen-3-yl-methylene)-8-thiophen-2-ylmethyl-8-aza-bicyclo[3.2.1]octane;
8-(3-Methyl-thiophen-2-ylmethyl)-3-(phenyl-thiophen-3-yl-methylene)-8-aza-bicyclo[3.2.1]octane;
8-(5-Methyl-thiophen-2-ylmethyl)-3-(phenyl-thiophen-3-yl-methylene)-8-aza-bicyclo[3.2.1]octane;
3-[(8-Aza-bicyclo[3.2.1]oct-3-ylidene)-thiophen-3-yl-methyl]-phenol;
3-{[8-(3-Methyl-but-2-enyl)-8-aza-bicyclo[3.2.1]oct-3-ylidene]-thiophen-3-yl-methyl}-phenol;
3-[(8-Allyl-8-aza-bicyclo[3.2.1]oct-3-ylidene)-thiophen-3-yl-methyl]-phenol;
3-[(8-Phenethyl-8-aza-bicyclo[3.2.1]oct-3-ylidene)-thiophen-3-yl-methyl]-phenol;
3-{[8-(2-Methyl-benzyl)-8-aza-bicyclo[3.2.1]oct-3-ylidene]-thiophen-3-yl-methyl}-phenol;
3-{[8-(2-Chloro-benzyl)-8-aza-bicyclo[3.2.1]oct-3-ylidene]-thiophen-3-yl-methyl}-phenol;
3-[Thiophen-3-yl-(8-thiophen-2-ylmethyl-8-aza-bicyclo[3.2.1]oct-3-ylidene)-methyl]-phenol;
3-{[8-(3-Methyl-thiophen-2-ylmethyl)-8-aza-bicyclo[3.2.1]oct-3-ylidene]-thiophen-3-yl-methyl}-phenol;
3-{[8-(5-Methyl-thiophen-2-yl methyl)-8-aza-bicyclo[3.2.1]oct-3-ylidene]-thiophen-3-yl-methyl}-phenol;
4-{[8-(3-Methyl-but-2-enyl)-8-aza-bicyclo[3.2.1]oct-3-ylidene]-thiophen-3-yl-methyl}-phenol;
4-[(8-Phenethyl-8-aza-bicyclo[3.2.1]oct-3-ylidene)-thiophen-3-yl-methyl]-phenol;
4-{[8-(2-Methyl-benzyl)-8-aza-bicyclo[3.2.1]oct-3-ylidene]-thiophen-3-yl-methyl}-phenol;
4-{[8-(2-Chloro-benzyl)-8-aza-bicyclo[3.2.1]oct-3-ylidene]-thiophen-3-yl-methyl}-phenol;
4-[Thiophen-3-yl-(8-thiophen-2-ylmethyl-8-aza-bicyclo[3.2.1]oct-3-ylidene)-methyl]-phenol;
4-{[8-(3-Methyl-thiophen-2-ylmethyl)-8-aza-bicyclo[3.2.1]oct-3-ylidene]-thiophen-3-yl-methyl}-phenol; and
4-{[8-(5-Methyl-thiophen-2-ylmethyl)-8-aza-bicyclo[3.2.1]oct-3-ylidene]-thiophen-3-yl-methyl}-phenol.

and pharmaceutically acceptable enantiomers, solvates, diastereomers and salts thereof.

Embodiments of the present invention also include a compound selected from the group consisting of
3-[(8-Allyl-8-aza-bicyclo[3.2.1]oct-3-ylidene)-thiophen-3-yl-methyl]-phenol;
3-{[8-(2-Methyl-benzyl)-8-aza-bicyclo[3.2.1]oct-3-ylidene]-thiophen-3-yl-methyl}-phenol;
3-{[8-(2-Chloro-benzyl)-8-aza-bicyclo[3.2.1]oct-3-ylidene]-thiophen-3-yl-methyl}-phenol;
3-[Thiophen-3-yl-(8-thiophen-2-ylmethyl-8-aza-bicyclo[3.2.1]oct-3-ylidene)-methyl]-phenol;
3-{[8-(3-Methyl-thiophen-2-ylmethyl)-8-aza-bicyclo[3.2.1]oct-3-ylidene]-thiophen-3-yl-methyl}-phenol;
3-{[8-(5-Methyl-thiophen-2-ylmethyl)-8-aza-bicyclo[3.2.1]oct-3-ylidene]-thiophen-3-yl-methyl}-phenol;
4-{[8-(3-Methyl-but-2-enyl)-8-aza-bicyclo[3.2.1]oct-3-ylidene]-thiophen-3-yl-methyl}-phenol;
4-{[8-(2-Methyl-benzyl)-8-aza-bicyclo[3.2.1]oct-3-ylidene]-thiophen-3-yl-methyl}-phenol;
4-{[8-(2-Chloro-benzyl)-8-aza-bicyclo[3.2.1]oct-3-ylidene]-thiophen-3-yl-methyl}-phenol;
4-[Thiophen-3-yl-(8-thiophen-2-ylmethyl-8-aza-bicyclo[3.2.1]oct-3-ylidene)-methyl]-phenol; and
4-{[8-(5-Methyl-thiophen-2-ylmethyl)-8-aza-bicyclo[3.2.1]oct-3-ylidene]-thiophen-3-yl-methyl}-phenol.

and pharmaceutically acceptable enantiomers, solvates, diastereomers and salts thereof.

In another embodiment, the present invention is directed to a method for the treatment of a pharmacological condition in a subject in need thereof comprising administering to the subject a therapeutically effective amount of a compound of Formula (I) or (II). In particular, the method of treatment is directed to the treatment of pain.

Instant compounds of the invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharic or trifluoroacetic.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The compounds of this invention may be chiral and, thus, may exist as enantiomers. In addition, the compounds may exist as diastereomers. It is to be understood that all such enantiomers and diastereomers, as well as all mixtures thereof, are encompassed within the scope of the present invention.

Furthermore, some of the crystalline forms for the compounds may exist as polymorphs and as such are intended to be included in the present invention.

In addition, some of the compounds may form solvates with water (i.e., hydrates) or common organic solvents, and such solvates are also intended to be encompassed within the scope of this invention.

The compounds of the present invention may be used to treat mild to moderately severe pain in warm-blooded animals such as humans by administration of an analgesically effective dose. The dosage range would be from about 0.01 mg to about 15,000 mg, in particular from about 0.1 mg to about 3500 mg or, more particularly from about 0.1 mg to about 1000 mg of active ingredient in a regimen of about 1 to 4 times per day for an average (70 kg) human; although, it is apparent to one skilled in the art that the therapeutically effective amount for active compounds of the invention will vary as will the types of pain being treated.

Examples of pain intended to be within the scope of the present invention include, but are not limited to, centrally mediated pain, peripherally mediated pain, structural or soft tissue injury related pain, progressive disease related pain, neuropathic pain and acute pain such as caused by acute injury, trauma or surgery and chronic pain such as caused by neuropathic conditions, diabetic peripheral neuropathy, post-herpetic neuralgia, trigeminal neuralgia, post-stroke pain syndromes or cluster or migraine headaches.

The compounds of the present invention may also be used as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases. A therapeutically effective dose can be determined by persons skilled in the art by the use of established animal models. Such a dose would likely fall in the range of from about 0.01 mg to about 15,000 mg of active ingredient administered 1 to 4 times per day for an average (70 kg) human.

Pharmaceutical compositions of the invention comprise compounds of formulas (I) and (II) as defined above, particularly in admixture with a pharmaceutically acceptable carrier. Illustrative of the invention, therefore, is a pharmaceutical composition comprising a pharmaceutically acceptable carrier and any of the compounds described above. Another illustration of the invention is a pharmaceutical composition made by mixing any of the compounds described above and a pharmaceutically acceptable carrier. A further illustration of the invention is a process for making a pharmaceutical composition comprising mixing any of the compounds described above and a pharmaceutically acceptable carrier.

To prepare the pharmaceutical compositions of this invention, one or more compounds of the invention or salt thereof, as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

GENERAL SYNTHETIC METHODS

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

Scheme 1 describes a general scheme for the preparation of certain target phenyl-thiophen-3-yl-methanone derivatives of the invention using synthetic methods to prepare intermediate compounds also intended to be within the scope of the present invention.

Treatment of 1a with n-butyl lithium provides an intermediate 1b. Without isolating 1b, it can be directly added to substituted benzonitrile as shown in Scheme 1. Subsequent refluxing the crude with 2N HCl gives 1c. Alternatively, Compound 1c may also be prepared reversing the sequence. Treatment of bromophenyl with n-butyl lithium would result in phenyl lithium. Addition of 3-cyanothiophene to phenyl lithium and subsequent acid hydrolysis can also give 1c.

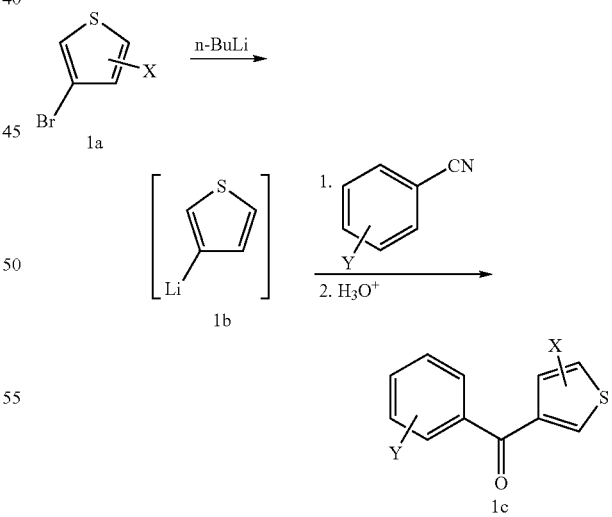

Scheme 1

The described method does not limit to phenyl-thiophen-3-yl-methanone. Various combinations, such as bromoheterocycle and cyanoheterocycle, and bromoheterocycle and benzonitrile, can be used to prepare compounds such as di-thiophen-3-yl-methanone 2d and furan-3-yl-phenyl-methanone 1e as shown in Scheme 2.

Scheme 2

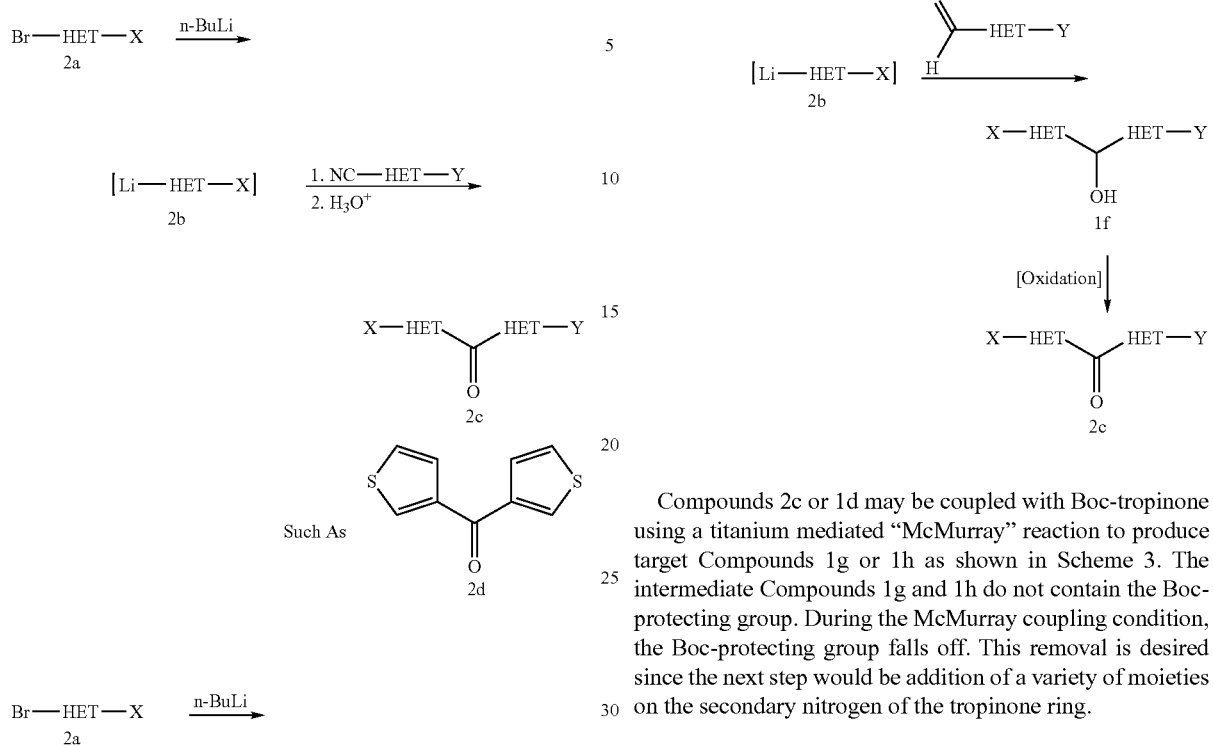

Alternately, the intermediate biaryl ketone may be prepared by the synthetic pathway shown in Scheme 3. Treatment of 2a with n-BuLi and subsequent addition of a heterocyclic aldehyde would provide a biaryl alcohol 1f. Oxidation of 1f using reagents like pyridinium chlorochromate would provide the ketone intermediate 2c.

Scheme 3

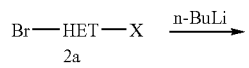

Compounds 2c or 1d may be coupled with Boc-tropinone using a titanium mediated "McMurray" reaction to produce target Compounds 1g or 1h as shown in Scheme 3. The intermediate Compounds 1g and 1h do not contain the Boc-protecting group. During the McMurray coupling condition, the Boc-protecting group falls off. This removal is desired since the next step would be addition of a variety of moieties on the secondary nitrogen of the tropinone ring.

As shown in Scheme 4, various functional groups can be added to the secondary nitrogen of the tropinone ring. Two widely used methods are nucleophilic displacement reaction and reductive alkylation. In nucleophilic displacement reaction, alkyl halides can be treated with 1g or 1h in the presence of base, such as potassium bicarbonate to give I or II. Using reductive alkylation, 1g or 1h would be treated with aldehydes in the presence of sodium triacetoxyborohydride, acetic acid, and trimethyl orthoformate to provide 1 or II.

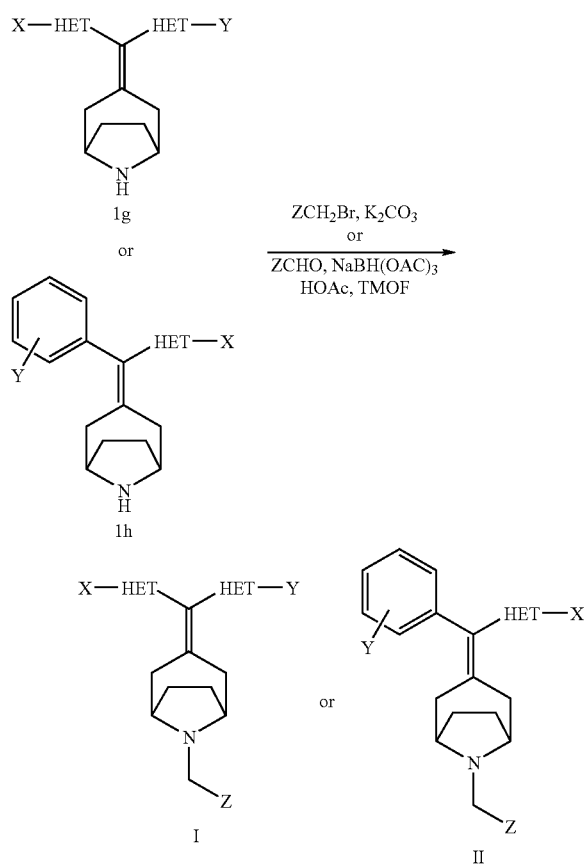

Scheme 4

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halogenhydrocarbon solvents. In those cases where the product is isolated as the acid addition salt the free base may be obtained by techniques known to those skilled in the art. In those cases in which the product is isolated as an acid addition salt, the salt may contain one or more equivalents of the acid.

Enantiomers of the compounds of the present invention may be separated using chiral HPLC.

Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

EXAMPLES

Compounds that are representative of this invention may be prepared as per the following examples offered by way of illustration and not by way of limitation. For the sake of clarity, bracketed numbers following compound names indicate the stoichiometric salt associated with the compound, which is further exemplified by the calculated analytical data. Also, examples specifically used to prepare intermediates for the further synthesis of compounds of the invention are designated by "Procedure." As well, instant compounds may also be used as starting materials in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Example 1

Phenyl-thiophen-3-yl-methanone

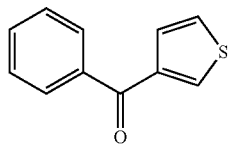

The solution containing 0.937 mL (10 mmol) of 3-bromothiophene, 3 mL of tetrahydrofuran, and 8 mL of ether was cooled to −78° C. under $N_2$. To the cooled solution was then added 4 mL of n-BuLi ([2.5] M in hexane) drop wise, while maintaining the reaction temperature below −70° C. The reaction solution turned to light yellow suspension. The suspension was allowed to stir 15 min at <−70° C. After 15 min, a solution containing 1.02 mL (10 mmol) of benzonitrile and 3 mL of tetrahydrofuran was added drop wise while maintaining the reaction temperature below −70° C. After the addition, the reaction suspension was allowed to stir 1 hr at −78° C. and slowly warmed to −10° C. over 2 hr. After 2 hr the reaction was stopped by adding 10 mL of $H_2O$ and 30 mL of 2N HCl. The aqueous solution was separated from the organic phase. The aqueous phase was washed with ether (2>20 mL). The washed aqueous solution was then heated to reflux for 2 hr. After 2 hr, the solution was cooled. To the cooled solution was added 30 mL of ether. The aqueous solution was removed. The organic solution was finally washed with brine, dried over $MgSO_4$, and concentrated under reduced pressure. The concentrated sample was purified by flashy chromatography (hexane:ethyl acetate, from 4 to 6 % ethyl acetate over 16 column volume) to obtain 1.36 gm (72.3%) of a clear oil; $^1$H NMR 300 MHz ($CDCl_3$) δ 7.93 (t, 1H), 7.83-7.86 (m, 2H), 7.26-7.61 (m, 5H).

Example 2

3-(Phenyl-thiophen-3-yl-methylene)-8-aza-bicyclo[3.2.1]octane

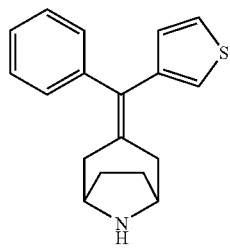

To 3.75 gm (57 mmol) of zinc powder in 40 mL of dry THF at −20° C. was carefully added 3.2 mL (29 mmol) of TiCl$_4$ under N$_2$. After the addition, the reaction mixture was allowed to heat to reflux and refluxed for 2 hr under N$_2$. The black reaction suspension was then cooled to room temperature. To the cooled reaction suspension was then slowly added a solution containing 1.35 g (7.2 mmol) phenyl-thiophen-3-yl-methanone, 1.62 g (7.2 mmol) boc-tropinone, and 8 mL of dry THF. Once the addition was complete, the reaction was allowed to reflux for 4 h. After 4 hr, the reaction mixture was cooled to room temperature. The cooled reaction mixture was filtered and the precipitates were washed with THF. The combined filtrates were concentrated. To the concentrated crude was then added 100 mL of 10% K$_2$CO$_3$ in H$_2$O and 150 mL of Et$_2$O. After removing the aqueous layer, the organic fraction was washed with brine, dried over MgSO$_4$, filtered, and concentrated to obtain 2.0 gm (~100% yield) of light yellow foam; MS m/z (MH$^+$) 292; $^1$H NMR 300 MHz (MeOD-d$_4$) δ 7.16-7.38 (m, 7H), 6.86-6.88 (dd, 1H), 3.99-4.06 (m, 2H), 2.52-2.83 (m, 4H), 1.93-2.08 (m, 4H).

Example 3

8-(3-Methyl-but-2-enyl)-3-(phenyl-thiophen-3-yl-methylene)-8-aza-bicyclo[3.2.1]octane

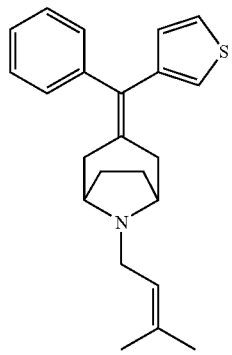

To 100 mg (355 µmol) of 3-(phenyl-thiophen-3-yl-methylene)-8-aza-bicyclo[3.2.1]octane in 1 mL of acetonitrile was added 98 mg (710 µmol) of K$_2$CO$_3$ and 41 µL (355 µmol) of 4-bromo-2-methyl-2-butene at room temperature. The reaction mixture was allowed to stir overnight at room temperature. Next day, the crude was filtered and washed with acetonitrile. The combined filtrates were concentrated. The concentrated sample was purified by reverse phase chromatography (20×100 mm J'sphere H-80 YMC column using a gradient of 0.1% TFA/water to 5% water/0.1% TFA/acetonitrile). The eluent was evaporated to yield the title compound as a white solid; MS m/z (MH$^+$) 350; $^1$H NMR 300 MHz (MeOD-d$_4$) δ 6.87-7.39 (m, 8H), 5.35 (t, 1H), 3.94-4.00 (m, 2H), 3.29-3.31 (m, 2H), 2.58-2.89 (m, 4H), 1.62-2.25 (m, 10H).

Example 4

8-Phenethyl-3-(phenyl-thiophen-3-yl-methylene)-8-aza-bicyclo[3.2.1]octane

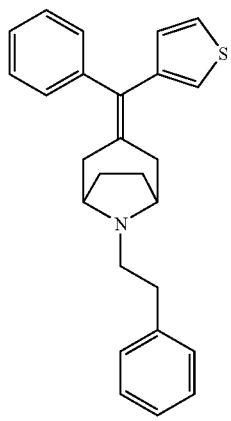

Following the protocol for Example 3 and substituting phenethyl bromide for 4-bromo-2-methyl-2-butene the title compound was obtained; MS m/z (MH$^+$) 386; $^1$H NMR 300 MHz (MeOD-d$_4$) δ 7.17-7.40 (m, 12H), 6.88-6.90 (m, 1H), 4.04-4.11 (m, 2H), 3.06-3.32 (m, 4H), 2.54-2.90 (m, 4H), 1.94-2.25 (m, 4H).

Example 5

8-(2-Methyl-benzyl)-3-(phenyl-thiophen-3-yl-methylene)-8-aza-bicyclo[3.2.1]octane

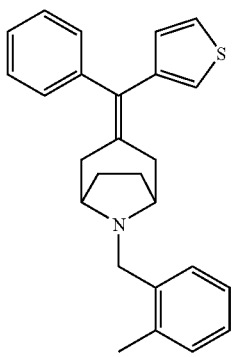

To 100 mg (355 µmol) of 3-(phenyl-thiophen-3-yl-methylene)-8-aza-bicyclo[3.2.1]octane in 1 mL of trimethyl orthoformate was added 62 µL (533 µmol) of 2-methylbenzaldehyde, 173 mg (817 µmol) of sodium triacetoxyborohydride, 34 µL of glacial acetic acid at room temperature. The reaction mixture was allowed to stir overnight at room temperature. Next day, the crude was diluted with 1 mL of dichloromethane and 0.5 mL of methanol. The diluted suspension was filtered and the precipitates were washed with dichloromethane. The combined filtrates were concentrated. The concentrated sample was purified by reverse phase chromatography (20×100 mm J'sphere H-80 YMC column using a gradient of 0.1% TFA/water to 5% water/0.1% TFA/acetonitrile). The eluent was evaporated to yield the title compound as a white solid; MS m/z (MH$^+$) 386; $^1$H NMR 300 MHz (MeOD-d$_4$) δ 6.86-7.51 (m, 12H), 4.26 (s, 2H), 4.05-4.11 (m, 2H), 2.03-2.89 (m, 11H).

Example 6

8-(2-Chloro-benzyl)-3-(phenyl-thiophen-3-yl-methylene)-8-aza-bicyclo[3.2.1]octane

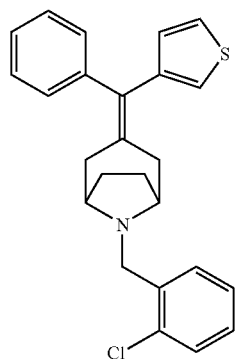

Following the protocol for Example 5 and substituting 2-chlorobenzaldehyde for 2-methylbenzaldehyde the title compound was obtained; MS m/z (MH$^+$) 407; $^1$H NMR 300 MHz (MeOD-d$_4$) δ 6.87-7.73 (m, 12H), 4.41 (s, 2H), 4.07-4.12 (m, 2H), 2.04-2.89 (m, 8H).

Example 7

3-(Phenyl-thiophen-3-yl-methylene)-8-thiophen-2-ylmethyl-8-aza-bicyclo[3.2.1]octane

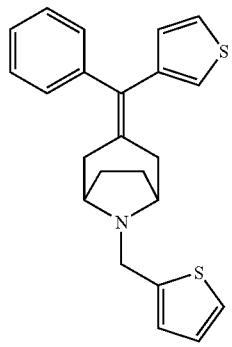

Following the protocol for Example 5 and substituting thiophene-2-carboxaldehyde for 2-methylbenzaldehyde the title compound was obtained; MS m/z (MH$^+$) 378; $^1$H NMR 300 MHz (MeOD-d$_4$) δ 7.62-7.63 (d, 1H), 7.13-7.36 (m, 9H), 6.86-6.88 (d, 1H), 4.48 (s, 2H), 3.96-4.04 (m, 2H), 2.00-2.90 (m, 8H).

Example 8

8-(3-Methyl-thiophen-2-ylmethyl)-3-(phenyl-thiophen-3-yl-methylene)-8-aza-bicyclo[3.2.1]octane

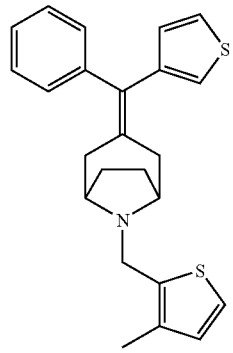

Following the protocol for Example 5 and substituting thiophene-3-methyl-2-carboxaldehyde for 2-methylbenzaldehyde the title compound was obtained; MS m/z (MH$^+$) 392; $^1$H NMR 300 MHz (MeOD-d$_4$) δ 7.51-7.53 (d, 1H), 7.15-7.37 (m, 7H), 6.97-6.99 (d, 1H), 6.87-6.88 (d, 1H), 4.40 (s, 2H), 4.03-4.10 (m, 2H), 2.02-2.90 (m, 11H).

Example 9

8-(5-Methyl-thiophen-2-ylmethyl)-3-(phenyl-thiophen-3-yl-methylene)-8-aza-bicyclo[3.2.1]octane

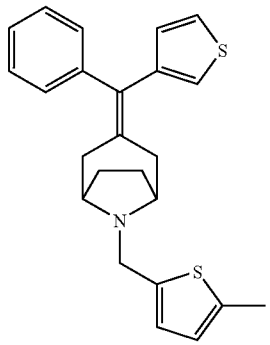

Following the protocol for Example 5 and substituting thiophene-5-methyl-2-carboxaldehyde for 2-methylbenzaldehyde the title compound was obtained; MS m/z (MH$^+$) 392; $^1$H NMR 300 MHz (MeOD-d$_4$) δ 7.11-7.38 (m, 8H), 6.86-6.88 (d, 1H), 6.80 (s, 1H), 4.37 (s, 2H), 3.96-4.02 (m, 2H), 2.02-2.90 (m, 11H).

Example 10

(3-Methoxy-phenyl)-thiophen-3-yl-methanone

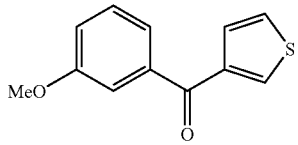

Following the protocol for Example 1 and substituting 3-methoxybenzonitrile for benzonitrile the title compound was obtained; $^1$H NMR 300 MHz (MeOD-d$_4$) δ 8.08-8.09 (dd, 1H), 7.17-7.62 (m, 6H), 3.85 (s, 3H).

Example 11

3-[(3-Methoxy-phenyl)-thiophen-3-yl-methylene]-8-aza-bicyclo[3.2.1]octane

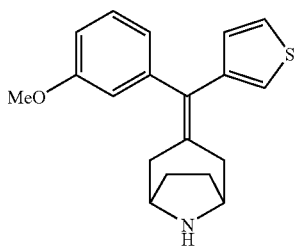

Following the protocol for Example 2 and substituting (3-methoxy-phenyl)-thiophen-3-yl-methanone for phenyl-thiophen-3-yl-methanone the title compound was obtained; MS m/z (MH$^+$) 312; $^1$H NMR 300 MHz (MeOD-d$_4$) δ 7.36-7.38 (dd, 1H), 7.24-7.30 (t, 1H), 7.17-7.18 (dd, 1H), 6.82-6.90 (m, 2H), 6.74-6.76 (d, 1H), 6.68-6.69 (d, 1H), 4.00-4.06 (m, 2H), 3.76 (s, 3H), 1.92-2.82 (m, 8H).

Example 12

8-Allyl-3-[(3-methoxy-phenyl)-thiophen-3-yl-methylene]-8-aza-bicyclo[3.2.1]octane

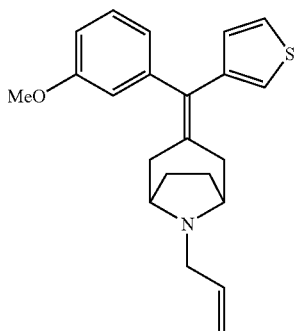

Following the protocol for Example 3 and substituting 3-[(3-methoxy-phenyl)-thiophen-3-yl-methylene]-8-aza-bicyclo[3.2.1]octane for 3-(phenyl-thiophen-3-yl-methylene)-8-aza-bicyclo[3.2.1]octane and allyl bromide for 4-bromo-2-methyl-2-butene, the title compound was obtained; MS m/z (MH$^+$) 352; $^1$H NMR 300 MHz (MeOD-d$_4$) δ 7.25-7.29 (dd, 1H), 7.17-7.22 (t, 1H), 7.01-7.03 (m, 1H), 6.83-6.84 (d, 1H), 6.75-6.78 (m, 1H), 6.72-6.75 (d, 1H), 6.65-6.70 (m, 1H), 5.85-5.99 (m,1H), 5.13-5.22 (m, 2H), 3.72 (s, 3H), 3.21-3.31 (m, 2H), 3.06-3.08 (d, 2H), 1.58-2.46 (m, 8H).

Example 13

3-[(3-Methoxy-phenyl)-thiophen-3-yl-methylene]-8-(3-methyl-but-2-enyl)-8-aza-bicyclo[3.2.1]octane

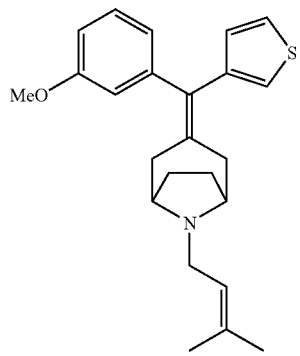

Following the protocol for Example 3 and substituting 3-[(3-methoxy-phenyl)-thiophen-3-yl-methylene]-8-aza-bicyclo[3.2.1]octane for 3-(phenyl-thiophen-3-yl-methylene)-8-aza-bicyclo[3.2.1]octane the title compound was obtained; MS m/z (MH$^+$) 380; $^1$H NMR 300 MHz (MeOD-d$_4$) δ 7.26-7.28 (dd, 1H), 7.17-7.22 (t, 1H), 7.01-7.03 (dd, 1H), 6.83-6.85 (dd, 1H), 6.75-6.78 (dd, 1H), 6.68-6.71 (d, 1H), 6.65-6.65 (d, 1H), 5.28-5.32 (m, 1H), 3.72 (s, 3H), 3.20-3.30 (m, 2H), 3,03-3.05 (d, 2H), 2.46 (s, 2H), 1.85-2,40 (m, 6H), 1.74 (s, 3H), 1.64 (s, 3H), 1.53-1.61 (m, 2H).

Example 14

3-[(3-Methoxy-phenyl)-thiophen-3-yl-methylene]-8-phenethyl-8-aza-bicyclo[3.2.1]octane

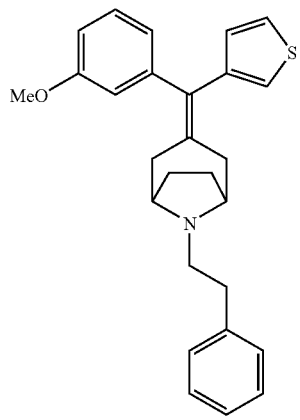

Following the protocol for Example 3 and substituting 3-[(3-methoxy-phenyl)-thiophen-3-yl-methylene]-8-aza-bicyclo[3.2.1]octane for 3-(phenyl-thiophen-3-yl-methylene)-8-aza-bicyclo[3.2.1]octane and phenethyl bromide for 4-bromo-2-methyl-2-butene the title compound was obtained; MS m/z (MH⁺) 417; ¹H NMR 300 MHz (MeOD-d₄) δ 7.12-7.32 (m, 7H), 7.01-7.02 (dd, 1H), 6.83-6.85 (dd, 1H), 6.75-6.78 (dd, 1H), 6.69-6.72 (d, 1H), 6.65-6.66 (m, 1H), 3.72 (s, 3H), 3.27-3.34 (m, 2H), 2.65-2.84 (m, 4H), 1.58-2.53 (m, 8H).

Example 15

3-[(3-Methoxy-phenyl)-thiophen-3-yl-methylene]-8-(2-methyl-benzyl)-8-aza-bicyclo[3.2.1]octane

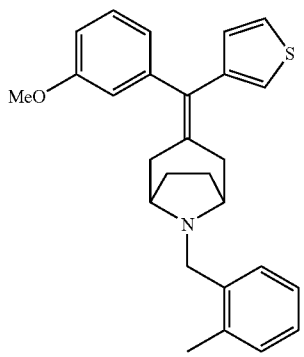

To 100 mg (321 μmol) of 3-[(3-Methoxy-phenyl)-thiophen-3-yl-methylene]-8-aza-bicyclo[3.2.1]octane in 1 mL of trimethyl orthoformate was added 56 μL (482 μmol) of 2-methylbenzaldehyde, 156 mg (739 μmol) of sodium triacetoxyborohydride, 34 μL of glacial acetic acid at room temperature. The reaction mixture was allowed to stir 10 days at room temperature. After 10 days, the crude was diluted with 1 mL of DCM and 0.5 mL of MeOH. The diluted solution was filtered and washed with 1 mL of DCM. The combined filtrates were concentrated. The concentrated sample was purified using Biotage NH₂-silica column using a gradient of 5% ethyl acetate/hexane to 40% ethyl acetate/hexane. The eluent was evaporated to yield 133 mg of the title compound as a white solid; MS m/z (MH⁺) 416.

Example 16

8-(2-Chloro-benzyl)-3-[(3-methoxy-phenyl)-thiophen-3-yl-methylene]-8-aza-bicyclo[3.2.1]octane

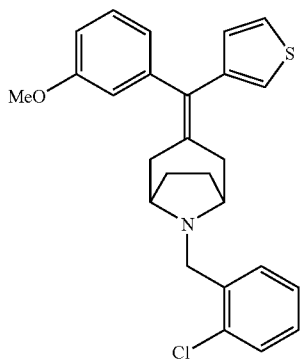

Following the protocol for Example 15 and substituting 2-chlorobenzaldehyde for 2-methylbenzaldehyde, the title compound was obtained; MS m/z (MH⁺) 437.

Example 17

3-[(3-Methoxy-phenyl)-thiophen-3-yl-methylene]-8-thiophen-2-ylmethyl-8-aza-bicyclo[3.2.1]octane

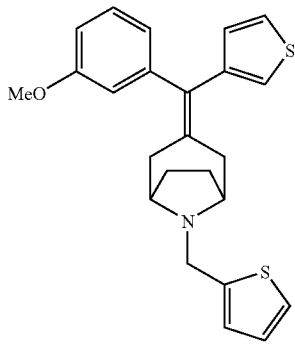

Following the protocol for Example 15 and substituting thiophene-2-carboxaldehyde for 2-methylbenzaldehyde, the title compound was obtained; MS m/z (MH⁺) 408.

Example 18

3-[(3-Methoxy-phenyl)-thiophen-3-yl-methylene]-8-(3-methyl-thiophen-2-ylmethyl)-8-aza-bicyclo[3.2.1]octane

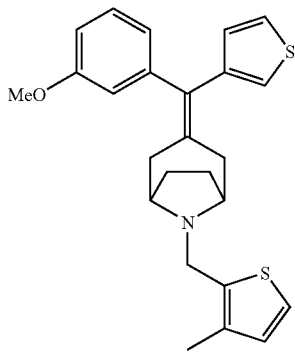

Following the protocol for Example 15 and substituting thiophene-3-methyl-2-carboxaldehyde for 2-methylbenzaldehyde, the title compound was obtained; MS m/z (MH⁺) 422.

Example 19

3-[(3-Methoxy-phenyl)-thiophen-3-yl-methylene]-8-(5-methyl-thiophen-2-ylmethyl)-8-aza-bicyclo[3.2.1]octane

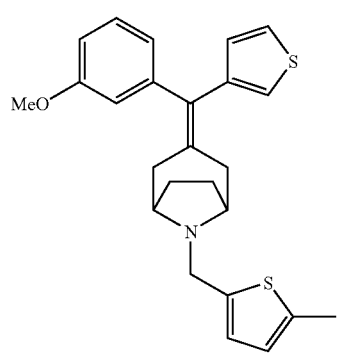

Following the protocol for Example 15 and substituting thiophene-5-methyl-2-carboxaldehyde for 2-methylbenzaldehyde, the title compound was obtained; MS m/z (MH+) 422.

Example 20

3-[(8-Aza-bicyclo[3.2.1]oct-3-ylidene)-thiophen-3-yl-methyl]-phenol

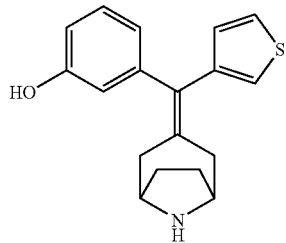

To 400 mg (1.05 mmol) of 3-[(3-methoxy-phenyl)-thiophen-3-yl-methylene]-8-(3-methyl-but-2-enyl)-8-aza-bicyclo[3.2.1]octane in 12 mL of dichloromethane at −78° C. was added 8.43 mL ([1M] in DCM) of boron tribromide drop wise. The reaction solution was slowly warmed to room temperature over 1 hr and allowed to stir 3 hr at room temperature. After 3 hr, to the reaction solution was added 20 mL of a saturated solution of NaHCO$_3$, and 20 mL of 20% ethanol in DCM. The aqueous phase was removed. The organic phase was washed with 20 mL of brine, dried over MgSO$_4$, and concentrated. The concentrated sample was purified by reverse phase chromatography (20×100 mm J'sphere H-80 YMC column using a gradient of 0.1% TFA/water to 5% water/0.1% TFA/acetonitrile). The eluent corresponding to 3-[(8-Aza-bicyclo[3.2.1]oct-3-ylidene)-thiophen-3-yl-methyl]-phenol (earlier eluent) was evaporated to yield 76 mg of the title compound as a white solid; MS m/z (MH+) 298; $^1$H NMR 300 MHz (MeOD-d$_4$) δ 7.34-7.36 (dd,1H), 7.13-7.18 (m, 2H), 6.86-6.88 (dd, 1H), 6.58-6.70 (m, 3H), 3.99-4.04 (m, 2H), 2.48-2.80 (m, 4H), 1.90-2.06 (m, 4H).

Example 21

3-{[8-(3-Methyl-but-2-enyl)-8-aza-bicyclo[3.2.1]oct-3-ylidene]-thiophen-3-yl-methyl}-phenol

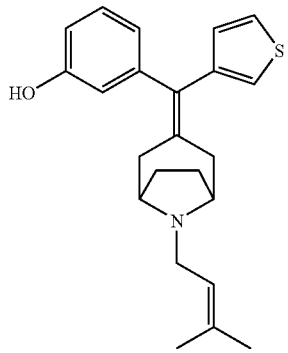

Following the protocol for Example 20, the eluent corresponding to 3-{[8-(3-methyl-but-2-enyl)-8-aza-bicyclo[3.2.1]oct-3-ylidene]-thiophen-3-yl-methyl}-phenol (later eluent) was evaporated to yield 83 mg of the title compound as a white solid; MS m/z (MH+) 366; $^1$H NMR 300 MHz (MeOD-d$_4$) δ 7.27-7.29 (m, 1H), 7.08-7.13 (t, 1H), 7.02-7.03 (m, 1 H), 6.83-6.85 (m, 1H), 6.56-6.65 (m, 3H), 5.31-5.33 (m, 1H), 3.25 - 3.32 (m, 2H), 3.05-3.07 (d, 2H), 2.30-2.61 (m, 4H), 1.96-2.04 (m, 2H), 1.75 (s, 3H), 1.66 (s, 3H), 1.61-1.65 (m, 2H).

Example 22

3-[(8-Allyl-8-aza-bicyclo[3.2.1]oct-3-ylidene)-thiophen-3-yl-methyl]-phenol

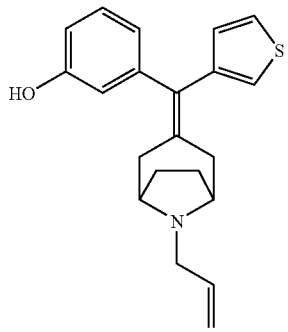

To 72 mg (0.20 mmol) of 8-allyl-3-[(3-methoxy-phenyl)-thiophen-3-yl-methylene]-8-aza-bicyclo[3.2.1]octane in 2 mL of dichloromethane at −78° C. was added 1.68 mL ([1 M] in DCM) of boron tribromide drop wise. The reaction solution was slowly warmed to room temperature over 1 hr and allowed to stir 3 hr at room temperature. After 3 hr, to the reaction solution was added 4 mL of a saturated solution of NaHCO$_3$, and 4 mL of 20% ethanol in DCM. The aqueous phase was removed. The organic phase was washed with 4 mL of brine, dried over MgSO$_4$, and concentrated. The concentrated sample was purified by reverse phase chromatography (20×100 mm J'sphere H-80 YMC column using a gradient of 0.1% TFA/water to 5% water/0.1% TFA/acetonitrile). The eluent corresponding to 3-[(8-allyl-8-azabicyclo[3.2.1]oct-3-ylidene)-thiophen-3-yl-methyl]-phenol was evaporated to yield 12 mg of the title compound as a white solid; MS m/z (MH$^+$) 338.

Example 23

3-[(8-Phenethyl-8-aza-bicyclo[3.2.1]oct-3-ylidene)-thiophen-3-yl-methyl]-phenol

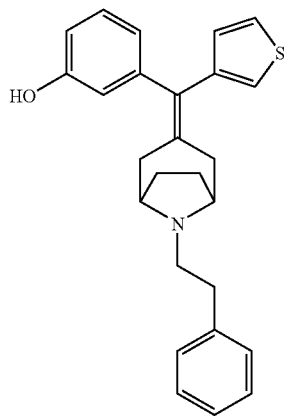

Following the protocol for Example 22 and substituting 3-[(3-methoxy-phenyl)-thiophen-3-yl-methylene]-8-phenethyl-8-aza-bicyclo[3.2.1]octane for 8-allyl-3-[(methoxy-phenyl)-thiophen-3-yl-methylene]-8-aza-bicyclo[3.2.1]octane, the eluent corresponding to 3-[(8-Phenethyl-8-aza-bicyclo[3.2.1]oct-3-ylidene)-thiophen-3-yl-methyl]-phenol was evaporated to yield 16 mg of the title compound as a white solid; MS m/z (MH$^+$) 402.

Example 24

3-{([8-(2-Methyl-benzyl)-8-aza-bicyclo[3.2.1]oct-3-ylidene]-thiophen-3-yl-methyl}-phenol

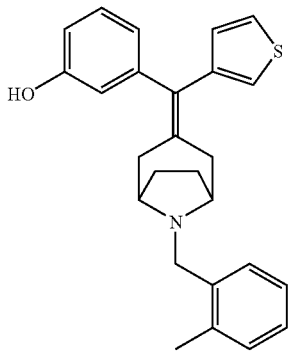

Following the protocol for Example 22 and substituting 3-[(3-methoxy-phenyl)-thiophen-3-yl-methylene]-8-(2-methyl-benzyl)-8-aza-bicyclo[3.2.1]octane for 8-allyl-3-[(3-methoxy-phenyl)-thiophen-3-yl-methylene]-8-aza-bicyclo[3.2.1]octane the title compound was obtained as a light tan solid; MS m/z (MH$^+$) 402.

Example 25

3-{[8-(2-Chloro-benzyl)-8-aza-bicyclo[3.2.1]oct-3-ylidene]-thiophen-3-yl-methyl}-phenol

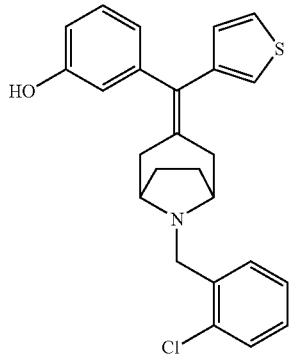

Following the protocol for Example 22 and substituting 8-(2-chloro-benzyl)-3-[(3-methoxy-phenyl)-thiophen-3-yl-methylene]-8-aza-bicyclo[3.2.1]octane for 8-allyl-3-[(3-methoxy-phenyl)-thiophen-3-yl-methylene]-8-aza-bicyclo[3.2.1]octane the title compound was obtained as a light tan solid; MS m/z (MH$^+$) 422; $^1$H NMR 300 MHz (MeOD-d$_4$) δ 7.70-7.72 (d, 1H), 7.47-7.60 (m, 3H), 7.35-7.38 (t, 1H), 7.13-7.19 (m, 2H), 6.87-6.89 (d, 1H), 6.58-6.70 (m, 3H), 4.41 (s, 2H), 4.00-4.12 (m, 2H), 1.93-2.87 (m, 8H).

Example 26

3-[Thiophen-3-yl-(8-thiophen-2-ylmethyl-8-aza-bicyclo[3.2.1]oct-3-ylidene)-methyl]-phenol

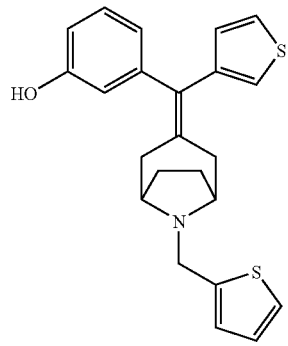

Following the protocol for Example 22 and substituting 3-[(3-methoxy-phenyl)-thiophen-3-yl-methylene]-8-thiophen-2-ylmethyl-8-aza-bicyclo[3.2.1]octane for 8-allyl-3-[(3-methoxy-phenyl)-thiophen-3-yl-methylene]-8-aza-bicyclo[3.2.1]octane, the title compound was obtained as a white solid; MS m/z (MH$^+$) 394.

Example 27

3-{[8-(3-Methyl-thiophen-2-ylmethyl)-8-aza-bicyclo[3.2.1]oct-3-ylidene]-thiophen-3-yl-methyl}-phenol

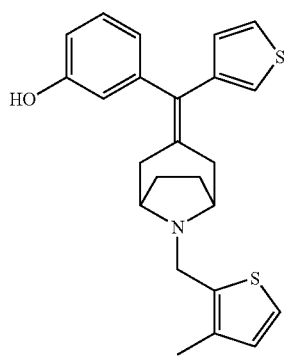

Following the protocol for Example 22 and substituting 3-[(3-methoxy-phenyl)-thiophen-3-yl-methylene]-8-(3-methyl-thiophen-2-yl methyl)-8-aza-bicyclo[3.2.1]octane for 8-allyl-3-[(3-methoxy-phenyl)-thiophen-3-yl-methylene]-8-aza-bicyclo[3.2.1]octane, the title compound was obtained as a white solid; MS m/z (MH$^+$) 408; $^1$H NMR 300 MHz (MeOD-d$_4$) δ 7.52-7.54 (d, 1H), 7.35-7.38 (t, 1H), 7.14-7.19 (m, 2H), 6.98-7.00 (d, 1H), 6.87-6.89 (d, 1H), 6.57-6.70 (m, 3H), 4.40 (s, 2H), 4.00-4.10 (m, 2H), 1.93-2.88 (m, 11H).

Example 28

3-{[8-(5-Methyl-thiophen-2-ylmethyl)-8-aza-bicyclo[3.2.1]oct-3-ylidene]-thiophen-3-yl-methyl}-phenol

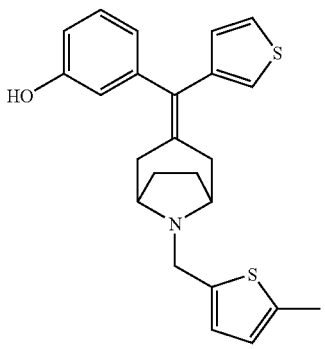

Following the protocol for Example 22 and substituting 3-[(methoxy-phenyl)-thiophen-3-yl-methylene]-8-(5-methyl-thiophen-2-ylmethyl)-8-aza-bicyclo[3.2.1]octane for 8-allyl-3-[(3-methoxy-phenyl)-thiophen-3-yl-methylene]-8-aza-bicyclo[3.2.1]octane, the title compound was obtained as a light green solid; MS m/z (MH$^+$) 408; $^1$H NMR 300 MHz (MeOD-d$_4$) δ 7.35-7.38 (dd, 1H), 7.11-7.19 (m, 3H), 6.87-6.88 (d, 1H), 6.80 (s, 1H), 6.57-6.70 (m, 3H), 4.37 (s, 2H), 3.97-4.05 (m, 2H), 1.93-2.88 (m, 11H).

Example 29

(4-Methoxy-phenyl)-thiophen-3-yl-methanone

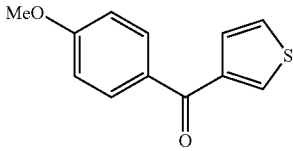

Following the protocol for Example 1 and substituting 4-methoxybenzonitrile for benzonitrile the title compound was obtained; $^1$H NMR 300 MHz (CDCl$_3$) δ 7.87-7.90 (m, 3H), 7.55-7.57 (dd, 1H), 7.36-7.39 (dd, 1H), 6.96-6.99 (m, 2H), 3.89 (s, 3H).

Example 30

3-[(4-Methoxy-phenyl)-thiophen-3-yl-methylene]-8-aza-bicyclo[3.2.1]octane

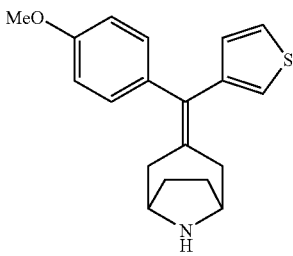

Following the protocol for Example 2 and substituting (4-methoxy-phenyl)-thiophen-3-yl-methanone for phenyl-thiophen-3-yl-methanone the title compound was obtained; MS m/z (MH$^+$) 312; $^1$H NMR 300 MHz (MeOD-d$_4$) δ 7.27-7.29 (m, 1 H), 6.80-7.03(m, 6H), 3.76 (s, 3H), 3.45-3.50 (m, 2H), 1.63-2.57 (m, 8 H).

Example 31

3-[(4-Methoxy-phenyl)-thiophen-3-yl-methylene]-8-(3-methyl-but-2-enyl)-8-aza-bicyclo[3.2.1]octane

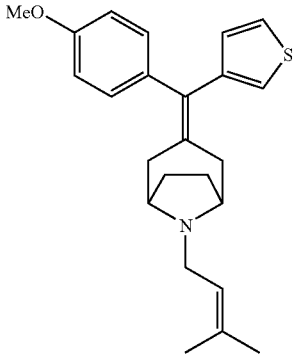

Following the protocol for Example 3 and substituting (4-methoxy-phenyl)-thiophen-3-yl-methanone for 3-(phenyl-thiophen-3-yl-methylene)-8-aza-bicyclo[3.2.1]octane, the title compound was obtained; MS m/z (MH$^+$) 380;

Example 32

3-[(4-Methoxy-phenyl)-thiophen-3-yl-methylene]-8-phenethyl-8-aza-bicyclo[3.2.1]octane

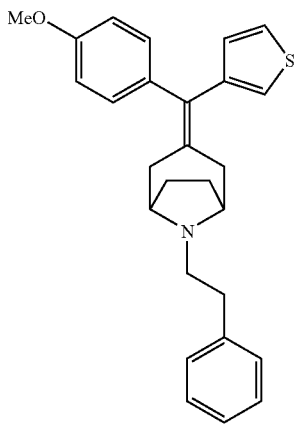

Following the protocol for Example 3 and substituting (4-methoxy-phenyl)-thiophen-3-yl-methanone for 3-(phenyl-thiophen-3-yl-methylene)-8-aza-bicyclo[3.2.1]octane and phenethyl bromide for 4-bromo-2-methyl-2-butene, the title compound was obtained; MS m/z (MH$^{-+}$) 416.

Example 33

3-[(4-Methoxy-phenyl)-thiophen-3-yl-methylene]-8-(2-methyl-benzyl)-8-aza-bicyclo[3.2.1]octane

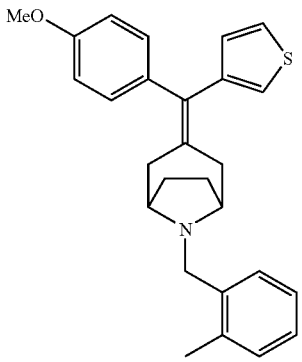

Following the protocol for Example 15 and substituting 3-[(4-methoxy-phenyl)-thiophen-3-yl-methylene]-8-aza-bicyclo[3.2.1]octane for 3-[(3-methoxy-phenyl)-thiophen-3-yl-methylene]-8-aza-bicyclo[3.2.1]octane, the title compound was obtained; MS m/z (MH$^+$) 437 MS m/z (MH$^+$) 416; $^1$H NMR 300 MHz (MeOD-d$_4$) δ 7.29 (7.33(m, 1H), 7.25-7.28 (dd, 1H), 6.75-7.19 (m, 9H), 3.75 (s, 3H), 3.58 (s, 2H), 3.20-3.31 (m, 2H), 2.16-2.58 (m, 7H), 2.00-2.02 (m, 2H), 1.59-1.66 (m, 2H).

Example 34

8-(2-Chloro-benzyl)-3-[(4-methoxy-phenyl)-thiophen-3-yl-methylene]-8-aza-bicyclo[3.2.1]octane

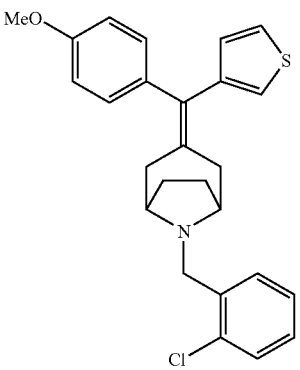

Following the protocol for Example 15, and substituting 3-[(4-methoxy-phenyl)-thiophen-3-yl-methylene]-8-aza-bicyclo[3.2.1]octane for 3-[(3-methoxy-phenyl)-thiophen-3-yl-methylene]-8-aza-bicyclo[3.2.1]octane and 2-chlorobenzaldehyde for 2-methylbenzaldehyde the title compound was obtained; MS m/z (MH$^+$) 437; $^1$H NMR 300 MHz (MeOD-d$_4$) δ 6.80-7.67 (m, 11H), 3.76 (s, 3H), 3.71 (s, 2H), 3.21-3.30 (m, 2H), 2.01-2.48 (m, 6H), 1.61-1.68 (m, 2H).

Example 35

3-[(4-Methoxy-phenyl)-thiophen-3-yl-methylene]-8-thiophen-2-ylmethyl-8-aza-bicyclo[3.2.1]octane

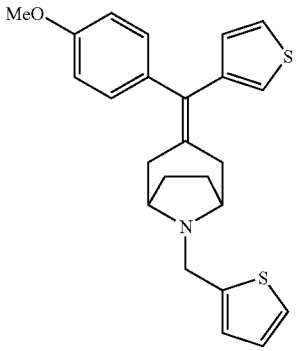

Following the protocol for Example 15, and substituting 3-[(4-methoxy-phenyl)-thiophen-3-yl-methylene]-8-aza-bicyclo[3.2.1]octane for 3-[(3-methoxy-phenyl)-thiophen-3-yl-methylene]-8-aza-bicyclo[3.2.1]octane and thiophene-2-carboxaldehyde for 2-methylbenzaldehyde the title compound was obtained; MS m/z (MH$^+$) 408; $^1$H NMR 300 MHz (CDCl$_3$) δ 6.81-7.29 (m, 10H), 3.79 (s, 2H), 3.78 (s, 3H), 3.24-3.33 (m, 2H), 2.22-2.54 (m, 4H), 1.91-2.04 (m, 2H), 1.58- 1.64 (m, 2H).

Example 36

3-[(4-Methoxy-phenyl)-thiophen-3-yl-methylene]-8-(3-methyl-thiophen-2-ylmethyl)-8-aza-bicyclo[3.2.1]octane

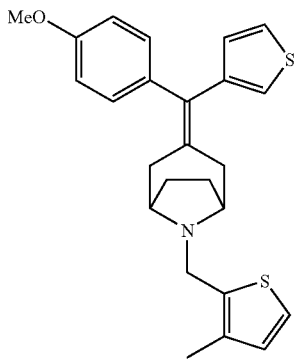

Following the protocol for Example 15, and substituting 3-[(4-methoxy-phenyl)-thiophen-3-yl-methylene]-8-aza-bicyclo[3.2.1]octane for 3-[(3-methoxy-phenyl)-thiophen-3-yl-methylene]-8-aza-bicyclo[3.2.1]octane and thiophene-3-methyl-2-carboxaldehyde for 2-methylbenzaldehyde the title compound was obtained; MS m/z (MH+) 423; $^1$H NMR 300 MHz (CDCl$_3$) δ 6.71-7.25 (m, 9H), 3.78 (s, 3H), 3.67 (s, 2H), 3.24-3.29 (m, 2H), 2.17-2.54 (m, 7H), 1.92-2.03 (m, 2H), 1.59-1.61 (m, 2H).

Example 37

3-[(4-Methoxy-phenyl)-thiophen-3-yl-methylene]-8-(5-methyl-thiophen-2-ylmethyl)-8-aza-bicyclo[3.2.1]octane

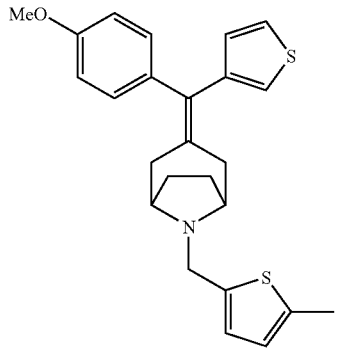

Following the protocol for Example 15, and substituting 3-[(4-methoxy-phenyl)-thiophen-3-yl-methylene]-8-aza-bicyclo[3.2.1]octane for 3-[(3-methoxy-phenyl)-thiophen-3-yl-methylene]-8-aza-bicyclo[3.2.1]octane and thiophene-5-methyl-2-carboxaldehyde 2-methylbenzaldehyde the title compound was obtained; MS m/z (MH+) 423; $^1$H NMR 300 MHz (CDCl$_3$) δ 7.17-7.19 (dd, 1H), 7.02-7.05 (m, 2H), 6.92-6.93 (dd, 1H), 6.80-6.83 (m, 3H), 6.66-6.67 (d, 2H) 6.54-6.55 (d, 2H), 3.78 (s, 3H), 3.71 (s, 2H), 3.32-3.35 (m, 2H), 2.24-2.57 (m, 7H), 1.89-1.92 (m, 2H), 1.57-1.59 (m, 2H).

Example 38

4-{[8-(3-Methyl-but-2-enyl)-8-aza-bicyclo[3.2.1]oct-3-ylidene]-thiophen-3-yl-methyl}-phenol

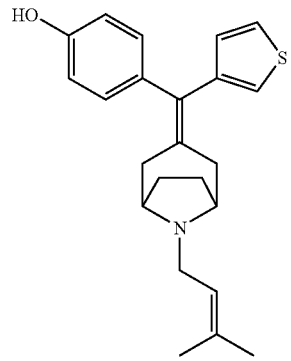

Following the protocol for Example 20, the eluent corresponding to 4-{[8-(3-methyl-but-2-enyl)-8-aza-bicyclo[3.2.1]oct-3-ylidene]-thiophen-3-yl-methyl}-phenol was evaporated to yield the title compound as a white solid; MS m/z (MH−)366.

Example 39

4-[(8Phenylethyl-8-aza-bicyclo[3.2.1]oct-3)ylidene)-thiophen-3-yl-methyl]-phenol

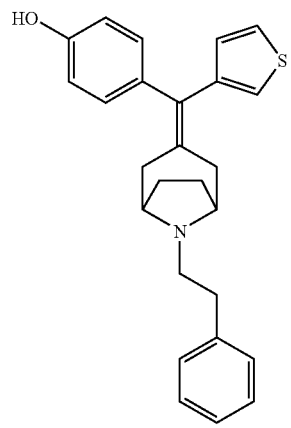

Following the protocol for Example 20, the eluent corresponding to 4-{[8-(3-methyl-but-2-enyl)-8-aza-bicyclo [3.2.1 ]oct-3-ylidene]-thiophen-3-yl-methyl}-phenol was evaporated to yield the title compound as a white solid; MS m/z (MH+) 402.

Example 40

4-{[8-(2-Methyl-benzyl)-8-aza-bicyclo[3.2.1]oct-3-ylidene]-thiophen-3-yl-methyl}-phenol

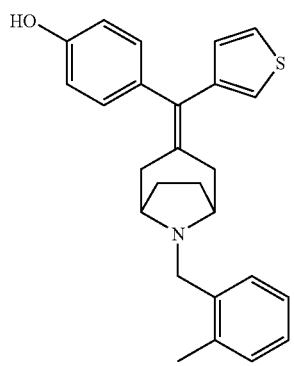

Following the protocol for Example 22 and substituting 3-[(4-methoxy-phenyl)-triophen-3-yl-methylene]-8-(2-methyl-benzyl)-8-aza-bicyclo[3.2.1]octane for 8-allyl-3-[(3-methoxy-phenyl)-thiophen-3-yl-methylene]-8-aza-bicyclo[3.2.1]octane, the title compound was obtained as a white solid; MS m/z (MH$^+$) 402.

Example 41

4-{[8-(2-Chloro-benzyl)-8-aza-bicyclo[3.2.1]oct-3-ylidene]-thiophen-3-yl-methyl}phenol

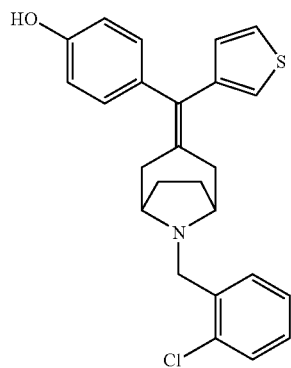

Following the protocol for Example 22 and substituting 8-(2-chloro-benzyl)-3-[(4-methoxy-phenyl)-thiophen-3-yl-methylene]-8-aza-bicyclo[3.2.1]octane for 8-allyl-3-[(3-methoxy-phenyl)-thiophen-3-yl-methylene]-8-aza-bicyclo[3.2.1]octane, the title compound was obtained as a white solid; MS m/z (MH$^+$) 422

Example 42

4-[Thiophen-3-yl-(8-thiophen-2-ylmethyl-8-aza-bicyclo[3.2.1]oct-3-ylidene)-methyl]phenol

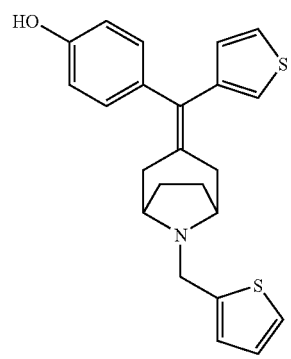

Following the protocol for Example 22 and substituting 3-[(4-methoxy-phenyl)-thiophen-3-yl-methylene]-8-thiophen-2-ylmethyl-8-aza-bicyclo[3.2.1]octane for 8-allyl-3-[(3-methoxy-phenyl)-thiophen-3-yl-methylene]-8-aza-bicyclo[3.2.1]octane, the title compound was obtained as a white solid; MS m/z (MH$^+$) 394.

Example 43

4-{[8-(3-Methyl-thiophen-2-ylmethyl)-8-aza-bicyclo[3.2.1]oct-3-ylidene]-thiophen-3-yl-methyl}-phenol

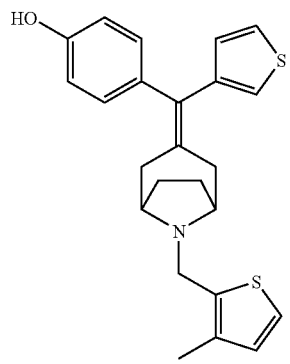

Following the protocol for Example 22 and substituting 3-[(4-methoxy-phenyl)-thiophen-3-yl-methylene]-8-(3-methyl-thiophen-2-ylmethyl)-8-aza-bicyclo[3.2.1]octane for 8-allyl-3-[(3-methoxy-phenyl)-thiophen-3-yl-methylene]-8-aza-bicyclo[3.2.1]octane, the title compound was obtained as a white solid; MS m/z (MH$^+$) 408; $^1$H NMR 300 MHz (MeOD-d$_4$) δ 7.52-7.53 (d, 1H), 7.34-7.37 (m, 1H), 7.14-7.14 (d, 1H), 6.95-6.99 (m, 3H), 6.84-6.86 (d, 1H), 6.74-6.76 (d, 2H), 4.40 (s, 2H), 4.04-4.14 (m, 2H), 1.93-2.87 (m, 11 H).

Example 44

4-{[8-(5-Methyl-thiophen-2-ylmethyl)-8-aza-bicyclo[3.2.1]oct-3-ylidene]-thiophen-3-yl-methyl}-phenol

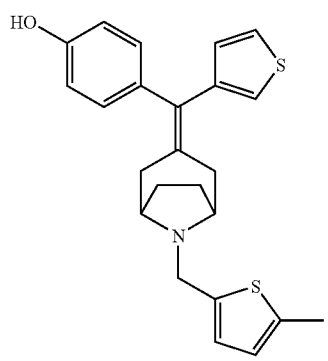

Following the protocol for Example 22 and substituting 3-[(4-methoxy-phenyl)-thiophen-3-yl-methylene]-8-(5-methyl-thiophen-2-ylmethyl)-8-aza-bicyclo[3.2.1]octane for 8-allyl-3-[(3-methoxy-phenyl)-thiophen-3-yl-methylene]-8-aza-bicyclo[3.2.1]octane, the title compound was obtained as a white solid; MS m/z (MH$^+$) 408; $^1$H NMR 300 MHz (MeOD-d$_4$) δ 7.34-7.37 (dd, 1H), 7.11-7.12 (m, 2H), 6.95-6.98 (d, 2H), 6.84-6.85 (d, 1H), 6.73-6.80 (m, 3H), 4.36 (s, 2H), 3.96-4.06 (m, 2H), 2.59-2.87 (m, 7H), 2.33-2.50 (m, 2H), 1.93-2.00 (m, 2H).

Example 45

Di-thiophen-3-yl-methanol

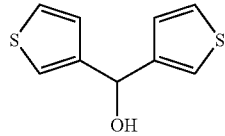

The solution containing 1.87 mL (20 mmol) of 3-bromothiophene, 3 mL of tetrahydrofuran, and 10 mL of ether was cooled to −78° C. under $N_2$. To the cooled solution was then added 8 mL of n-BuLi ([2.5] M in hexane) drop wise, while maintaining the reaction temperature below −70° C. The reaction solution turned to white cloudy. The suspension was allowed to stir 15 min at <−70° C. After 15 min, a solution containing 1.75 mL (20 mmol) of 2-thiophenecarboxaldehyde and 3 mL of tetrahydrofuran was added drop wise while maintaining the reaction temperature below −70° C. After the addition, the reaction suspension was allowed to stir 1 hr at −78° C. and slowly warmed to −10° C. over 2 hr. After 2 hr, the reaction was stopped by adding 50 mL of a saturated solution of $NH_4Cl$ and 100 mL of dichloromethane. The aqueous solution was separated from the organic phase. After removing the aqueous layer, the organic layer was washed with brine, dried over $MgSO_4$, and concentrated under reduced pressure. The concentrated sample was purified by flashy chromatography (hexane:ethyl acetate, from 10 to 15% ethyl acetate over 16 column volume) to obtain 2.12 gm (53.9%) of yellow solids; $^1$H NMR 500 MHz ($CDCl_3$) δ 7.29 (d, 1H), 7.29 (d, 1H), 7.22 (t, 1H), 7.21 (t, 1H), 7.05 (d, 1H), 7.04 (d, 1H), 5.97 (d, 1H), 2.22 (d, 1 H).

Example 46

Di-thiophen-3-yl-methanone

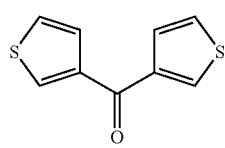

To 2.1 gm (10.7 mmol) of Di-thiophen-3-yl-methanol in 50 mL of dichloromethane at room temperature was added 3.0 gm (13.9 mmol) of PCC. The reaction suspension was allowed to stir 2 hrs at room temperature. After 2 hrs, the reaction mixture was filtered and precipitates were washed with dichloromethane. The combined filtrates were concentrated. The concentrated sample was purified by flashy chromatography (hexane:ethyl acetate, from 11 to 18% ethyl acetate over 16 column volume) to obtain 1.83 gm (88.0%) of light yellow crystals; $^1$H NMR 500 MHz ($CDCl_3$) δ 8.02 (d, 1H), 8.01 (d, 1H), 7.62 (d, 1H), 7.61 (d, 1H), 7.40 (d, 1H), 7.38 (d, 1H).

Example 47
3-(Di-thiophen-3-yl-methylene)-8-aza-bicyclo[3.2.1]octane

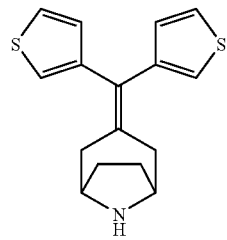

Following the protocol for Example 2 and substituting di-thiophen-3-yl-methanone for phenyl-thiophen-3-yl-methanone the title compound was obtained; MS m/z ($MH^+$) 288; $^1$H NMR 400 MHz (MeOD-$d_4$) δ 7.39 (d, 1H), 7.37 (d, 1H), 7.17 (t, 1H), 7.15 (t, 1H), 6.88 (d, 1H), 6.87 (d, 1H), 4.04 (m, 2H), 2.59-2.76 (m, 4H), 1.84-2.09 (m, 4H).

Example 48
3-(Di-thiophen-3-yl-methylene)-8-(3-methyl-but-2-enyl)-8-aza-bicyclo[3.2.1]octane

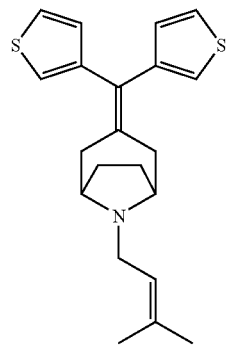

Following the protocol for Example 3 and substituting 3-(di-thiophen-3-yl-methylene)-8-aza-bicyclo[3.2.1]octane for 3-(phenyl-thiophen-3-yl-methylene)-8-aza-bicyclo[3.2.1]octane the title compound was obtained; MS m/z ($MH^+$) 356; $^1$H NMR 400 MHz (MeOD-$d_4$) δ 7.39 (d, 1 H), 7.38 (d, 1H), 7.18 (m, 2H), 6.90 (m, 2H), 5.36 (m, 1H), 3.98 (m, 2H), 3.63 (d, 2H), 2.64-2.84 (m, 4H), 1.93-2.28 (m, 4H), 1.86 (s, 3H), 1.79 (s, 3H).

Example 49
3-(Di-thiophen-3-yl-methylene)-8-thiophen-2-ylmethyl-8-aza-bicyclo[3.2.1]octane

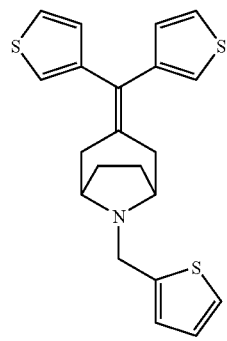

Following the protocol for Example 5, and substituting 3-(di-thiophen-3-yl-methylene)-8-aza-bicyclo[3.2.1]octane for 3-(phenyl-thiophen-3-yl-methylene)-8-aza-bicyclo[3.2.1]octane and thiophene-2-carboxaldehyde for 2-methyl-benzaldehyde the title compound was obtained; MS m/z (MH$^+$) 384; $^1$H NMR 400 MHz (MeOD-d$_4$) δ 7.60 (m, 1H), 7.35-7.38 (m, 3H), 7.12-7.22 (m, 3H), 6.87 (m, 2H), 4.47 (s, 2H), 3.98 (m, 2H), 2.65-2.82 (m, 4H), 1.94-200 (m, 4H).

Example 50

3-(Hydroxy-thiophen-3-yl-methyl)-benzonitrile

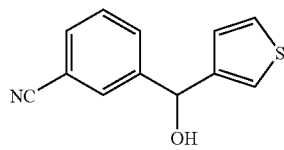

Following the protocol for Example 45, and substituting 3-cyanobenzaldehyde for 2-thiophenecarboxaldehyde the title compound was obtained; $^1$H NMR 500 MHz (CDCl$_3$) δ 7.72 (m, 1H), 7.58 (m, 1H), 7.56 (m, 1H), 7.45 (m, 1H), 732 (m, 1H), 7.21 (m, 1H), 6.96 (m, 1H), 5.93 (d, 1H), 2.04 (s, 1H).

Example 51

3-(Thiophene-3-carbonyl)-benzonitrile

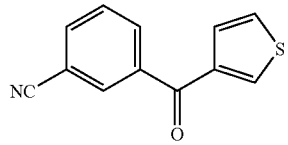

Following the protocol for Example 46, and substituting 3-(hydroxy-thiophen-3-yl-methyl)-benzonitrile for di-thiophen-3-yl-methanol the title compound was obtained; $^1$H NMR 500 MHz (CDCl$_3$) δ 8.12 (m, 1H), 8.07 (m, 1H), 7.94 (m, 1H), 7.87 (m, 1H), 7.62 (m, 1H), 7.59 (m, 1H), 7.45 (m, 1H).

Example 52

3-(Thiophene-3-carbonyl)-benzamide

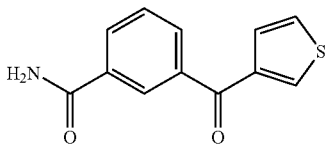

To 1.0 g (4.69 mmol) of 3-(thiophene-3-carbonyl)-benzonitrile in 8 mL of a concentrated NH$_4$OH at room temperature was added 6 mL of 30% H$_2$O$_2$ drop-wise. The white reaction mixture was allowed to stir overnight at room temperature. Next day, to the reaction crude was added 60 mL of a saturated solution of NaHCO$_3$ and 60 mL of ethyl acetate. After removing the aqueous layer, the organic layer was washed with brine, dried over Na$_2$SO$_4$, and concentrated. The concentrated crude was purified by flashy chromatography (dichloromethane:methanol, from 2 to 6% methanol over 16 column volume, then from 6 to 10% methanol over 5 column volume) to obtain 840 mg (77.8% yield) of white solids; $^1$H NMR 500 MHz (CDCl$_3$) δ 8.27 (m, 2H), 8.15 (m, 2H), 7.93 (m, 1H), 7.74 (m, 1H), 7.65 (t, 1H), 7.55 (m, 2H).

Example 53

3-[(8-Aza-bicyclo[3.2.1]oct-3-ylidene)-thiophen-3-yl-methyl]-benzamide

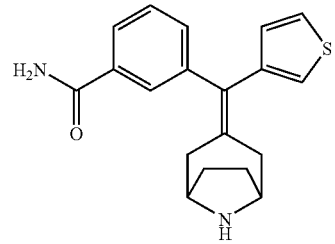

Following the protocol for Example 2 and substituting 3-(thiophene-3-carbonyl)-benzamide for phenyl-thiophen-3-yl-methanone the title compound was obtained; MS m/z (MH$^+$) 325; $^1$H NMR 400 MHz (MeOD-d$_4$) δ 7.78 (m, 1H), 7.71 (t, 1H), 7.34-7.50 (m, 3H), 7.21 (m, 1H), 6.90 (m, 1H), 4.00-4.08 (m, 2H), 2.44-2.84 (m, 4H), 1.84-2.19 (m, 4H).

Example 54

3-{[8-(3-Methyl-but-2-enyl)-8-aza-bicyclo[3.2.1]oct-3-ylidene]-thiophen-3-yl-methyl}-benzamide

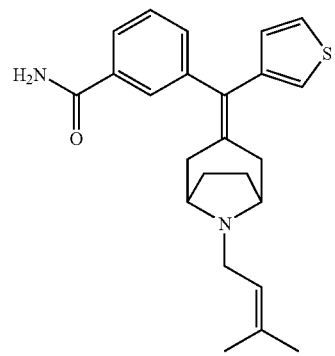

Following the protocol for Example 3 and substituting 3-[(8-aza-bicyclo[3.2.1]oct-3-ylidene)-thiophen-3-yl-methyl]-benzamide for 3-(phenyl-thiophen-3-yl-methylene)-8-aza-bicyclo[3.2.1]octane the title compound was obtained; MS m/z (MH$^+$) 393; $^1$H NMR 400 MHz (MeOD-d$_4$) δ 7.71 (m, 2H), 7.47 (t, 1 H), 7.35-7.41 (m, 2H), 7.22 (m, 1H), 6.90 (m, 1H), 5.35 (m, 1H), 3.94-4.02 (m, 2H), 3.63 (d, 2H), 2.49-2.90 (m, 4H), 1.96-2.33 (m, 4H), 1.86 (s, 3H), 1.78 (s, 3H).

Example 55

3-[Thiophen-3-yl-(8-thiophen-2-ylmethyl-8-aza-bicyclo[3.2.1]oct-3-ylidene)-methyl]-benzamide

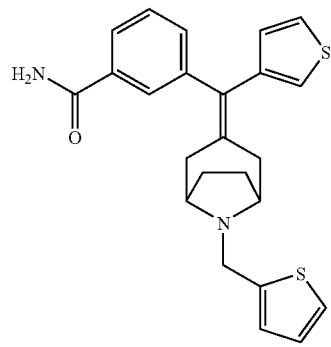

Following the protocol for Example 5, and substituting 3-[(8-aza-bicyclo[3.2.1]oct-3-ylidene)-thiophen-3-yl-methyl]-benzamide for 3-(phenyl-thiophen-3-yl-methylene)-8-aza-bicyclo[3.2.1]octane and thiophene-2-carboxaldehyde for 2-methylbenzaldehyde the title compound was obtained;

MS m/z (MH$^+$) 421; $^1$H NMR 400 MHz (MeOD-d$_4$) δ 7.78 (d, 1H), 7.71 (s, 1H), 7.62 (d, 1H), 7.46 (t, 1H), 7.35-7.40 (m, 3H), 7.22 (d, 1H), 7.14 (m, 1H), 6.89 (d, 1H), 4.48 (s, 2H), 3.90-4.04 (m, 2H), 2.50-2.90 (m, 4H), 2.37-2.40 (m, 2H), 2.01-2.06 (m, 2H).

BIOLOGICAL EXAMPLES

Screening Assay for δ-Opioid and μ-Opioid Receptor Binding

Rat Brain δ-Opioid Receptor Binding Assay

The activity of the compounds of the invention as analgesics was demonstrated by the rat brain δ-opioid receptor binding assay as described below.

Procedure

Male, Wistar rats (150-250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the δ-opioid binding assays. Following incubation with the δ-selective peptide ligand [$^3$H]DPDPE at 25° C., the tube contents are filtered through Whatman GF/B filter sheets on a Brandel cell harvester. The tubes and filters are rinsed three times with 4 mL of 10 mM HEPES (pH 7.4), and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a K$_i$ value (when a range of concentrations is tested).

% Inhibition was calculated as follows:

$$1 - \left( \frac{\text{(test compound dpm} - \text{nonspecific dpm)}}{\text{(total dpm} - \text{nonspecific dpm)}} \right) \times 100\%$$

K$_i$ value is calculated using the LIGAND (Munson, P. J. and Rodbard, D., Anal. Biochem. 107: 220-239,1980) data analysis program.

Rat Brain μ-Opioid Receptor Binding Assay

Procedure

Male, Wistar rats (150-250 g, VAF, Charles River, Kingston, N.Y.) are killed by cervical dislocation and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the μ-opioid binding assays. Following incubation with the m-selective peptide ligand [$^3$H]DAMGO at 25° C., the tube contents are filtered through Whatman GF/B filter sheets on a Brandel cell harvester. The tubes and filters are rinsed three times with 4 mL of 10 mM HEPES (pH 7.4) and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a K$_i$ value (when a range of concentrations is tested).

% Inhibition is calculated as follows:

$$1 - \left( \frac{\text{(test compound dpm} - \text{nonspecific dpm)}}{\text{(total dpm} - \text{nonspecific dpm)}} \right) \times 100\%$$

K$_i$ value is calculated using the LIGAND (Munson, P. J. and Rodbard, D., Anal. Biochem. 107:220-239, 1980) data analysis program.

Table 3 shows the biological activity (in K$_i$ value) for 10 nM solutions of certain of the present compounds as measured in the rat brain δ-opioid receptor binding assay and in the rat brain μ-opioid receptor binding assay. Table 3 also shows the ratio of the μ-opioid receptor binding to the δ-opioid receptor binding for those compounds.

TABLE 3

| Example | Ki (nM) δ | Ki (nM) μ | Ki (nM) μ/δ |
|---|---|---|---|
| 2 | 68.00 | 902.0 | 13.27 |
| 3 | 21.10 | 177.0 | 8.37 |
| 4 | 903.00 | 265.0 | 0.29 |
| 5 | 193.00 | 4110.0 | 21.28 |
| 6 | 229.00 | 1310.0 | 0.57 |
| 7 | 62.60 | 418.0 | 6.69 |
| 8 | 38.30 | 1520.0 | 3.96 |
| 9 | 38.80 | 413.0 | 10.66 |
| 20 | 6.27 | 24.7 | 3.93 |
| 21 | 0.91 | 7.1 | 7.8 |
| 22 | 1.69 | 26.0 | 15.6 |
| 23 | 437.00 | 37.0 | 0.08 |
| 24 | 5.96 | 48.6 | 8.15 |
| 25 | 1.69 | 34.2 | 20.22 |
| 26 | 0.17 | 5.4 | 31.78 |
| 27 | 5.85 | 30.4 | 5.20 |
| 28 | 1.65 | 12.6 | 7.65 |
| 38 | 5.37 | 93.0 | 17.3 |
| 39 | 397.00 | 166.0 | 0.42 |
| 40 | 35.70 | 64.8 | 1.82 |
| 41 | 12.50 | 36.5 | 2.91 |
| 42 | 2.92 | 89.2 | 30.54 |
| 43 | 31.40 | 187.0 | 5.94 |
| 44 | 9.04 | 75.2 | 8.33 |

What is claimed is:

1. A compound of formula (I)

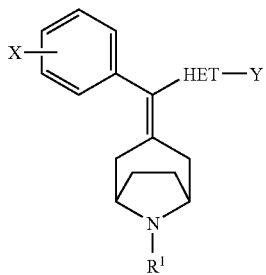

I

Wherein

HET is a 5-membered cyclic heteroalkanyl containing 1-2 heteroatoms independently selected from the group consisting of N, O and S; a 6-membered cyclic heteroalkanyl containing 1-3 heteroatoms independently selected from the group consisting of N, O and S; a 5-membered heteroaryl containing 1-2 heteroatoms independently selected from the group consisting of N, O and S; or a 6-membered heteroaryl containing 1-3 heteroatoms independently selected from the group consisting of N, O and S; wherein the point of attachment of HET to the rest of the molecule is through a ring carbon atom;

X and Y are one to three substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylcarbonylamino, $C_{1-6}$alkanylthio, $C_{1-6}$alkanylsulfonyl, halogen, hydroxy, cyano, hydroxycarbonyl, tetrazolyl, fluoroalkanyl and fluoroalkanyloxy; or X and Y taken together may form a bridge of 1 or 2 atoms selected from the group consisting of O, S, $CH_2$ and $-N(R^2)-$ wherein $R^2$ is $C_{1-6}$alkyl;

$R^1$ is selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl,cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoroalkanyl, thioureido, and fluoroalkanyloxy; alternatively, when phenyl and heteroaryl are optionally substituted with two substituents attached to adjacent carbon atoms, the two substituents can together form a single fused moiety; wherein the fused moiety is selected from the group consisting of $-(CH_2)_{3-5}-$ and $-O(CH_2)_{1-3}O-$;

and pharmaceutically acceptable enantiomers, diastereomers and salts thereof.

2. A compound of Formula (I) of claim 1 wherein HET is thienyl.

3. A compound of Formula (I) of claim 1 wherein HET is thien-3-yl.

4. A compound of Formula (I) of claim 1 wherein X is hydroxyl.

5. A compound of Formula (I) of claim 1 wherein Y is hydrogen.

6. A compound of Formula (I) of claim 1 wherein $R^1$ is heteroaryl($C_{1-8}$)alkanyl optionally substituted with one to three substituents independently selected from the group consisting of $C_{16}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoroalkanyl, thioureido, and fluoroalkanyloxy.

7. The compound of claim 6 wherein said heterorayl is thienyl.

8. The compound of claim 6 wherein said thienyl is unsubstituted.

9. The compound of claim 6 wherein said thienyl is thien-2-yl.

10. A compound selected from the group consisting of
3-(Phenyl-thiophen-3-yl-methylene)-8-aza-bicyclo[3.2.1]octane;
8-(3-Methyl-but-2-enyl)-3-(phenyl-thiophen-3-yl-methylene)-8-aza-bicyclo[3.2.1]octane;
8-Phenethyl-3-(phenyl-thiophen-3-yl-methylene)-8-aza-bicyclo[3.2.1]octane;
8-(2-Methyl-benzyl)-3-(phenyl-thiophen-3-yl-methylene)-8-aza-bicyclo[3.2.1]octane;
8-(2-Chloro-benzyl)-3-(phenyl-thiophen-3-yl-methylene)-8-aza-bicyclo[3.2.1]octane;
3-[(3-Methoxy-phenyl)-thiophen-3-yl-methylene]-8-aza-bicyclo[3.2.1]octane;
8-Allyl-3-[(3-methoxy-phenyl)-thiophen-3-yl-methylene]-8-aza-bicyclo[3.2.1]octane;
3-[(3-Methoxy-phenyl)-thiophen-3-yl-methylene]-8-(3-methyl-but-2-enyl)-8-aza-bicyclo[3.2.1]octane;
3-[(3-Methoxy-phenyl)-thiophen-3-yl-methylene]-8-phenethyl-8-aza-bicyclo[3.2.1]octane;
3-[(3-Methoxy-phenyl)-thiophen-3-yl-methylene]-8-(2-methyl-benzyl)-8-aza-bicyclo[3.2.1]octane;

8-(2-Chloro-benzyl)-3-[(3-methoxy-phenyl)-thiophen-3-yl-methylene]-8-aza-bicyclo[3.2.1]octane;

3-[(8-Aza-bicyclo[3.2.1]oct-3-ylidene)-thiophen-3-yl-methyl]-phenol;

3-{[8-(3-Methyl-but-2-enyl)-8-aza-bicyclo[3.2.1]oct-3-ylidene]-thiophen-3-yl-methyl}-phenol;

3-[(8-Allyl-8-aza-bicyclo[3.2.1]oct-3-ylidene)-thiophen-3-yl-methyl]-phenol;

3-[(8-Phenethyl-8-aza-bicyclo[3.2.1]oct-3-ylidene)-thiophen-3-yl-methyl]-phenol;

3-{[8-(2-Methyl-benzyl)-8-aza-bicyclo[3.2.1]oct-3-ylidene]-thiophen-3-yl-methyl}-phenol;

3-{[8-(2-Chloro-benzyl)-8-aza-bicyclo[3.2.1]oct-3-ylidene]-thiophen-3-yl-methyl}-phenol;

3-[(4-Methoxy-phenyl)-thiophen-3-yl-methylene]-8-aza-bicyclo[3.2.1]octane;

3-[(4-Methoxy-phenyl)-thiophen-3-yl-methylene]-8-(3-methyl-but-2-enyl)-8-aza-bicyclo[3.2.1]octane;

3-[(4-Methoxy-phenyl)-thiophen-3-yl-methylene]-8-phenethyl-8-aza-bicyclo[3.2.1]octane;

3-[(4-Methoxy-phenyl)-thiophen-3-yl-methylene]-8-(2-methyl-benzyl)-8-aza-bicyclo[3.2.1]octane;

8-(2-Chloro-benzyl)-3-[(4-methoxy-phenyl)-thiophen-3-yl-methylene]-8-aza-bicyclo[3.2.1]octane;

4-{[8-(3-Methyl-but-2-enyl)-8-aza-bicyclo[3.2.1]oct-3-ylidene]-thiophen-3-yl-methyl}-phenol;

4-[(8-Phenethyl-8-aza-bicyclo[3.2.1]oct-3-ylidene)-thiophen-3-yl-methyl]-phenol;

4-{[8-(2-Methyl-benzyl)-8-aza-bicyclo[3.2.1]oct-3-ylidene]-thiophen-3-yl-methyl}-phenol;

4-{[8-(2-Chloro-benzyl)-8-aza-bicyclo[3.2.1]oct-3-ylidene]-thiophen-3-yl-methyl}-phenol;

and pharmaceutically acceptable enantiomers, diastereomers and salts thereof.

11. A compound selected from the group consisting of 3-(Phenyl-thiophen-3-yl-methylene)-8-aza-bicyclo[3.2.1]octane;

8-(3-Methyl-but-2-enyl)-3-(phenyl-thiophen-3-yl-methylene)-8-aza-bicyclo[3.2.1]octane;

8-Phenethyl-3-(phenyl-thiophen-3-yl-methylene)-8-aza-bicyclo[3.2.1]octane;

8-(2-Methyl-benzyl)-3-(phenyl-thiophen-3-yl-methylene)-8-aza-bicyclo[3.2.1]octane;

8-(2-Chloro-benzyl)-3-(phenyl-thiophen-3-yl-methylene)-8-aza-bicyclo[3.2.1]octane;

3-[(8-Aza-bicyclo[3.2.1]oct-3-ylidene)-thiophen-3-yl-methyl]-phenol;

3-{[8-(3-Methyl-but-2-enyl)-8-aza-bicyclo[3.2.1]oct-3-ylidene]-thiophen-3-yl-methyl}-phenol;

3-[(8-Allyl-8-aza-bicyclo[3.2.1]oct-3-ylidene)-thiophen-3-yl-methyl]-phenol;

3-[(8-Phenethyl-8-aza-bicyclo[3.2.1]oct-3-ylidene)-thiophen-3-yl-methyl]-phenol;

3-{[8-(2-Methyl-benzyl)-8-aza-bicyclo[3.2.1]oct-3-ylidene]-thiophen-3-yl-methyl}-phenol;

3-{[8-(2-Chloro-benzyl)-8-aza-bicyclo[3.2.1]oct-3-ylidene]-thiophen-3-yl-methyl}-phenol;

4-{[8-(3-Methyl-but-2-enyl)-8-aza-bicyclo[3.2.1]oct-3-ylidene]-thiophen-3-yl-methyl}-phenol;

4-[(8-Phenethyl-8-aza-bicyclo[3.2.1]oct-3-ylidene)-thiophen-3-yl-methyl]-phenol;

4-{[8-(2-Methyl-benzyl)-8-aza-bicyclo[3.2.1]oct-3-ylidene]-thiophen-3-yl-methyl}-phenol; and 4-{[8-(2-Chloro-benzyl)-8-aza-bicyclo[3.2.1]oct-3-ylidene]-thiophen-3-yl-methyl}-phenol;

and pharmaceutically acceptable enantiomers, diastereomers and salts thereof.

12. A compound selected from the group consisting of

3-[(8-Allyl-8-aza-bicyclo[3.2.1]oct-3-ylidene)-thiophen-3-yl-methyl]-phenol;

3-{[8-(2-Methyl-benzyl)-8-aza-bicyclo[3.2.1]oct-3-ylidene]-thiophen-3-yl-methyl}-phenol;

3-{[8-(2-Chloro-benzyl)-8-aza-bicyclo[3.2.1]oct-3-ylidene]-thiophen-3-yl-methyl}-phenol;

4-{[8-(3-Methyl-but-2-enyl)-8-aza-bicyclo[3.2.1]oct-3-ylidene]-thiophen-3-yl-methyl}-phenol;

4-{[8-(2-Methyl-benzyl)-8-aza-bicyclo[3.2.1]oct-3-ylidene]-thiophen-3-yl-methyl}-phenol; and 4-{[8-(2-Chloro-benzyl)-8-aza-bicyclo[3.2.1]oct-3-ylidene]-thiophen-3-yl-methyl}-phenol;

and pharmaceutically acceptable enantiomers, diastereomers and salts thereof.

* * * * *